(12) United States Patent
Wempe et al.

(10) Patent No.: US 12,043,601 B2
(45) Date of Patent: Jul. 23, 2024

(54) N-SUBSTITUTED-1H-1,2,4-TRIAZOLE-3-CARBOXAMIDES, ANALOGUES THEREOF, AND METHODS OF TREATMENT USING SAME

(71) Applicants: THE REGENTS OF THE UNIVERSITY OF COLORADO, Denver, CO (US); NATIONAL JEWISH HEALTH, Denver, CO (US)

(72) Inventors: Michael Fitzpatrick Wempe, Aurora, CO (US); Andres Vazquez-Torres, Denver, CO (US); Shaodong Dai, Englewood, CO (US)

(73) Assignees: The Regents of the University of Colorado, Denver, CO (US); National Jewish Health, Denver, CO (US)

( * ) Notice: Subject to any disclaimer, the term of this patent is extended or adjusted under 35 U.S.C. 154(b) by 714 days.

(21) Appl. No.: 17/269,725

(22) PCT Filed: Aug. 22, 2019

(86) PCT No.: PCT/US2019/047637
§ 371 (c)(1),
(2) Date: Feb. 19, 2021

(87) PCT Pub. No.: WO2020/041556
PCT Pub. Date: Feb. 27, 2020

(65) Prior Publication Data
US 2021/0309618 A1 Oct. 7, 2021

Related U.S. Application Data

(60) Provisional application No. 62/721,392, filed on Aug. 22, 2018.

(51) Int. Cl.
  *C07D 249/14* (2006.01)
  *A61P 31/04* (2006.01)
  *C07D 403/12* (2006.01)
  *C07D 405/12* (2006.01)

(52) U.S. Cl.
  CPC .......... *C07D 249/14* (2013.01); *A61P 31/04* (2018.01); *C07D 403/12* (2013.01); *C07D 405/12* (2013.01)

(58) Field of Classification Search
CPC .. C07D 249/14; C07D 403/12; C07D 405/12; A61P 31/04
See application file for complete search history.

(56) References Cited

U.S. PATENT DOCUMENTS

| | | | |
|---|---|---|---|
| 3,927,216 A | 12/1975 | Witkowski et al. | |
| 4,006,159 A | 2/1977 | Newman | |
| 2006/0079485 A1 | 4/2006 | Yedgar et al. | |
| 2009/0264342 A1 | 10/2009 | Cottarel et al. | |
| 2011/0301180 A1* | 12/2011 | Collman ................... | A61P 9/04 544/242 |

FOREIGN PATENT DOCUMENTS

WO  WO-9743277 A1 * 11/1997 .............. A61P 31/00

OTHER PUBLICATIONS

Dong et al. Evaluation of Novel Antibacterial N-Halamine Nanoparticles Prodrugs towards Susceptibility of *Escherichia coli* Induced by DksA Protein, Molecules, 20, 7292-7308. (Year: 2015).*
Moriarty et al, *Escherichia coli* induces platelet aggregation in an FcγRIIA-dependent manner, Journal of Thrombosis and Haemostasis, 14, 797-806. (Year: 2015).*
International Preliminary Report on Patentability for International (PCT) Patent Application No. PCT/US2019/047637, dated Mar. 4, 2021 7 pages.
International Search Report and Written Opinion prepared by the United States Patent Office on Nov. 27, 2019, for International Application No. PCT/US2019/047637.

* cited by examiner

*Primary Examiner* — Matthew P Coughlin
*Assistant Examiner* — Meghan C Heasley
(74) *Attorney, Agent, or Firm* — Sheridan Ross P.C.

(57) ABSTRACT

The present invention relates to the discovery of novel N-(substituted)-1H-1,2,4-triazole-3-carboxamide compounds capable of inhibiting DksA activity in a bacteria cell. In certain embodiments, the compounds are capable of killing or weakening bacteria. In another aspect, the invention relates to methods of treating bacterial infection in a subject in need thereof, the method comprising administering to the subject a compound of the invention.

10 Claims, 10 Drawing Sheets

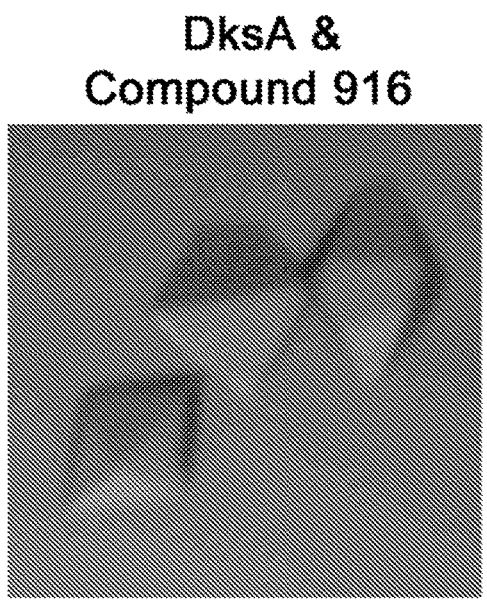
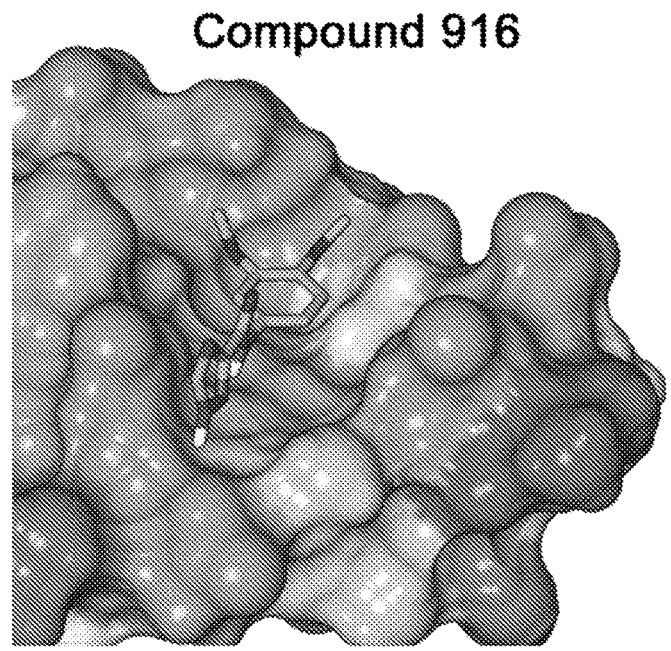
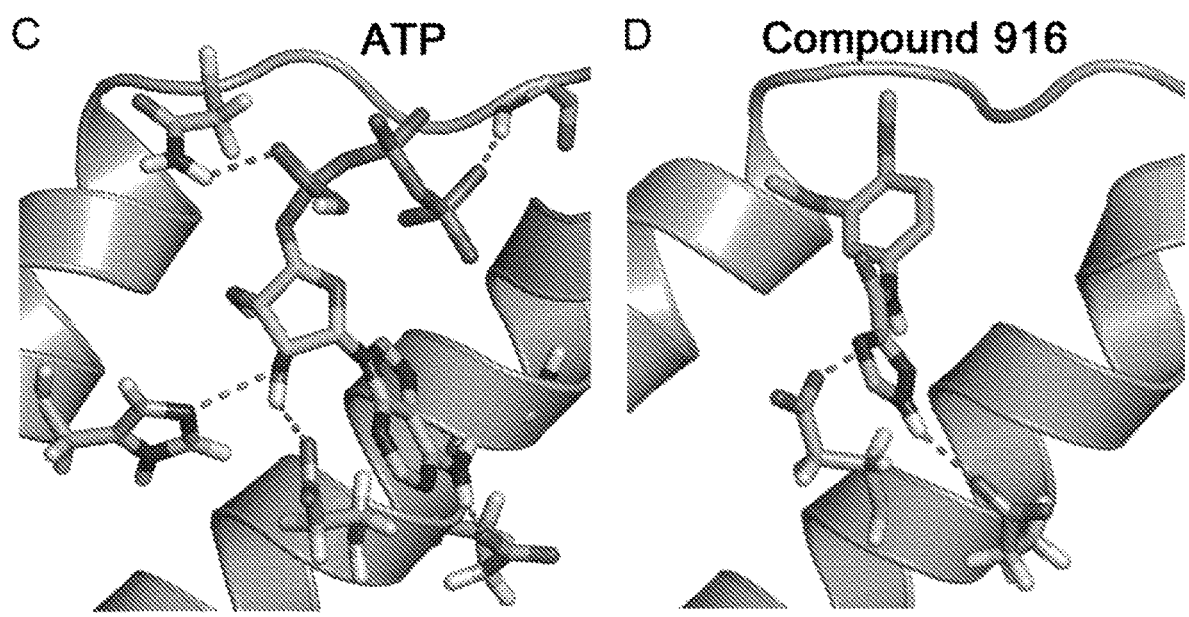
FIG. 2A
FIG. 2B
FIG. 2C
FIG. 2D

N-SUBSTITUTED-1H-1,2,4-TRIAZOLE-3-CARBOXAMIDES, ANALOGUES THEREOF, AND METHODS OF TREATMENT USING SAME

CROSS-REFERENCE TO RELATED APPLICATIONS

This application is a national stage application under 35 U.S.C. 371 and claims the benefit of PCT Application No. PCT/US2019/047637 having an international filing date of 22 Aug. 2019, which designated the United States, and which PCT application claimed the benefit of priority under 35 U.S.C. § 119(e) to U.S. Provisional Patent Application Ser. No. 62/721,392, filed 22 Aug. 2018, the entire disclosures of each of which are incorporated herein by reference.

STATEMENT REGARDING FEDERALLY SPONSORED RESEARCH OR DEVELOPMENT

This invention was made with government support under grant number BX0002073 awarded by Veterans Affairs. The government has certain rights in the invention.

BACKGROUND OF THE INVENTION

RNA polymerase-binding transcription factor DksA is a transcription factor protein that acts by binding directly to RNA polymerase (RNAP). DksA is required for negative regulation of rRNA expression and positive regulation of several amino acid biosynthesis promoters. DksA is highly conserved among Gram-negative bacteria, making this protein a potential target for small molecule antibiotics. At the tip of the coiled-coil domain, DksA contains a pocket with Asp and Glu residues that serve as a potential ligand binding pocket and drugable site. Inhibition of DksA by a small molecule could serve as a method of weakening or killing a virulent bacteria.

There remains a need in the art for compounds and methods of treating bacterial infection. In certain embodiments, the compounds and methods can target bacterial DksA protein, inhibiting its activity, thereby weakening and/or killing the bacteria. The present invention meets these needs.

BRIEF DESCRIPTION OF THE DRAWINGS

The following detailed description of specific embodiments of the invention will be better understood when read in conjunction with the appended drawings. For the purpose of illustrating the invention, there are shown in the drawings specific embodiments. It should be understood, however, that the invention is not limited to the precise arrangements and instrumentalities of the embodiments shown in the drawings.

FIG. 1A is a graph showing the high conservation of several acidic residues at the tip of the coiled-coil domain of DksA homologues from diverse Gram-negative bacteria. FIG. 1B is a graph showing that Compound 916 (N-(3,4-dimethoxyphenyl)-1H-1,2,4-triazole-3-carboxamide, prior art) has excellent activity against DksA-mediated repression of rpsM in vitro transcription. FIG. 1C is a graph showing that Compound 916 inhibits intracellular growth of Salmonella in J774 macrophage-like cells. The dash line represents intracellular growth of ΔdksA Salmonella. FIG. 1D is a graph showing that the addition (+) of 16 μg/ml of Compound 916 inhibits the intracellular expression of the SPI2 effector sifA FIGS. 2A-2D are images showing the binding of drug to the pocket at the tip of DksA coiled-coil domain. FIG. 2A is an image of co-crystals of Salmonella recombinant DksA protein and compound 916. FIG. 2B is an in silico model of E. coli DksA protein (PDB 1TJL) with compound 916 docked into the putative compound-binding site at the tip of the coiled-coil. The surface of DksA is depicted in shades of darker gray and lighter gray for most hydrophilic and hydrophobic, respectively. FIGS. 2C and 2D are in silico model images showing the predicted interactions of ATP (FIG. 2C) and compound 916 (FIG. 2D) with DksA pocket residues, depicted as dashed lines.

FIG. 8A is a graph showing peritoneal mouse macrophages pretreated with interferon-γ and exposed to wild-type Salmonella or ΔdksA. FIG. 8B is a graph showing survival percentage of infected cells following treatment with compounds #6 and #21 compared with wild-type Salmonella or ΔdksA cells.

DETAILED DESCRIPTION OF THE INVENTION

Figure 1A:
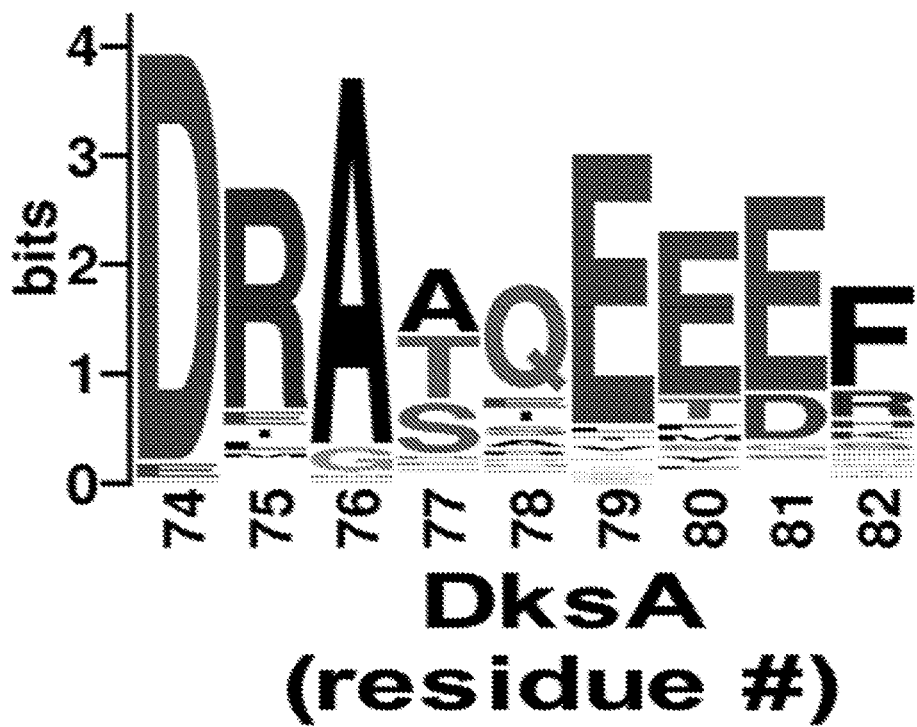
FIGS. 1A-1D are graphs showing drug activity against DksA.
Figure 1B:
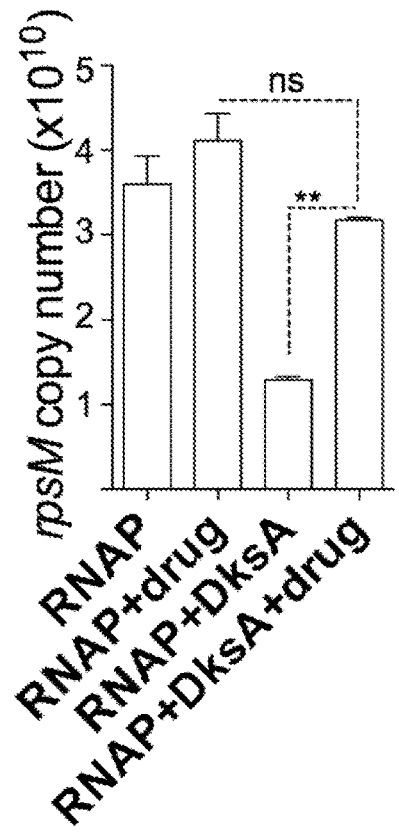

The present invention relates to the discovery of novel N-(substituted)-1H-1,2,4-triazole-3-carboxamides and analogues thereof, which are capable of inhibiting DksA activity in a bacterium. In certain embodiments, the compounds are capable of killing or weakening bacteria. In another aspect, the invention relates to methods of treating bacterial infection in a subject in need thereof, the method comprising administering to the subject a compound of the invention.

Compounds

In one aspect, the invention provides a compound of Formula (I), or a salt, solvate, enantiomer, diastereoisomer or tautomer thereof:

(I)

wherein:
L¹ is selected from the group consisting of a bond, $C_{1-6}$ alkylene optionally substituted with at least one selected from the group consisting of halogen and $C_1$-$C_6$ alkyl;
L² is selected from the group consisting of a bond and —CH₂—;
X is selected from the group consisting of H,

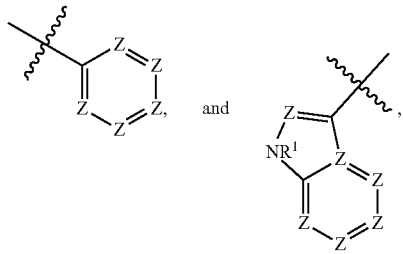

wherein each instance of Z is independently selected from the group consisting of N and CR¹, provided that 0-2 occurrences of Z are N;
Y is selected from the group consisting of

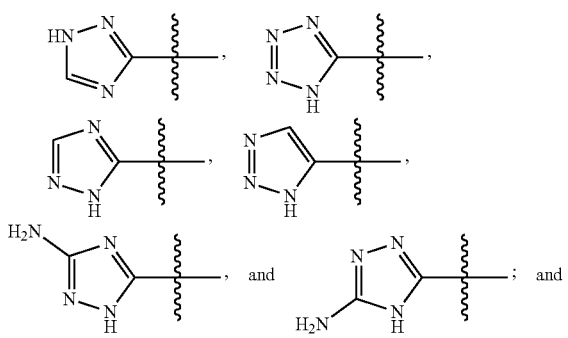

each instance of R¹ is independently selected from the group consisting of H, —OH, halogen, $C_{1-6}$ alkyl, $C_{1-6}$ haloalkyl, $C_{1-6}$ alkoxy, $C_{1-6}$ haloalkoxy, $C_{3-8}$ cycloalkyl, and $C_{1-6}$ perhaloalkyl, or two adjacent R¹ groups are taken together to form a 4-6 membered homocyclic or heterocyclic fused ring (such as for example, cyclopentyl, cyclohexyl, 1,3-dioxolane, or 1,3-dioxane).

In certain embodiments, the compound of Formula (I) is at least one compound selected from the group consisting of:

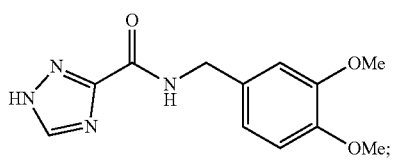

N-(3,4-dimethoxybenzyl)-1H-1,2,4-triazole-3-carboxamide

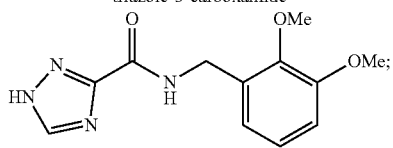

N-(2,3-dimethoxybenzyl)-1H-1,2,4-triazole-3-carboxamide

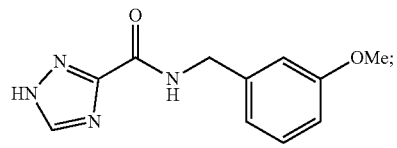

N-(3-methoxybenzyl)-1H-1,2,4-triazole-3-carboxamide

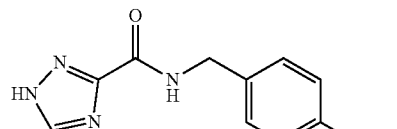

N-(4-methoxybenzyl)-1H-1,2,4-triazole-3-carboxamide

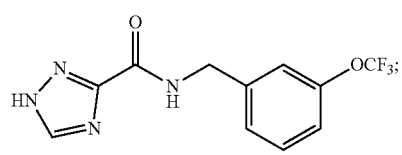

N-(3-(trifluoromethoxy)benzyl)-1H-1,2,4-triazole-3-carboxamide

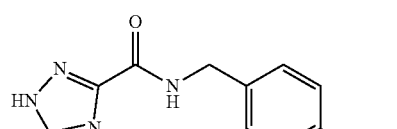

N-(4-(trifluoromethoxy)benzyl)-1H-1,2,4-triazole-3-carboxamide

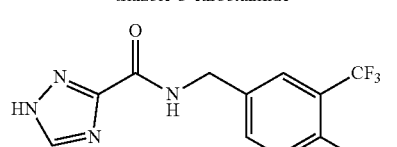

N-(4-methoxy-3-(trifluoromethoxy)benzyl)-1H-1,2,4-triazole-3-carboxamide

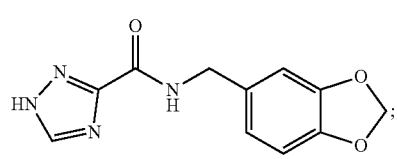

N-(benzo[d][1,3]dioxol-5-ylmethyl)-1H-1,2,4-triazole-3-carboxamide

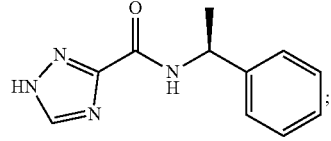

(S)-N-(1-phenylethyl)-1H-1,2,4-triazole-3-carboxamide

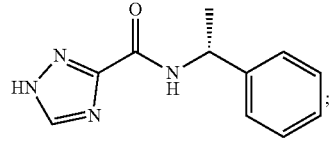

(R)-N-(1-phenylethyl)-1H-1,2,4-triazole-3-carboxamide

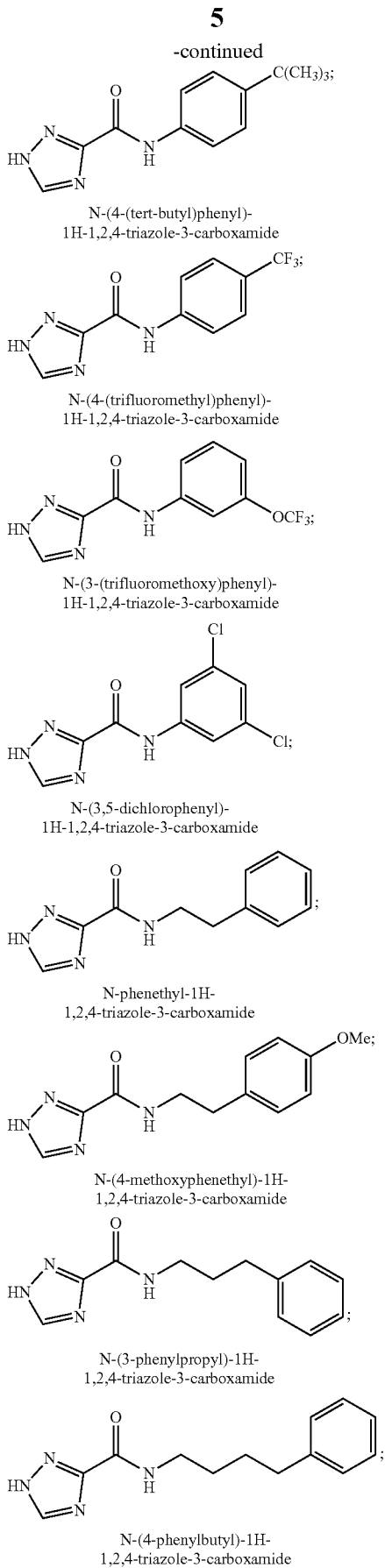

N-(4-(tert-butyl)phenyl)-1H-1,2,4-triazole-3-carboxamide

N-(4-(trifluoromethyl)phenyl)-1H-1,2,4-triazole-3-carboxamide

N-(3-(trifluoromethoxy)phenyl)-1H-1,2,4-triazole-3-carboxamide

N-(3,5-dichlorophenyl)-1H-1,2,4-triazole-3-carboxamide

N-phenethyl-1H-1,2,4-triazole-3-carboxamide

N-(4-methoxyphenethyl)-1H-1,2,4-triazole-3-carboxamide

N-(3-phenylpropyl)-1H-1,2,4-triazole-3-carboxamide

N-(4-phenylbutyl)-1H-1,2,4-triazole-3-carboxamide

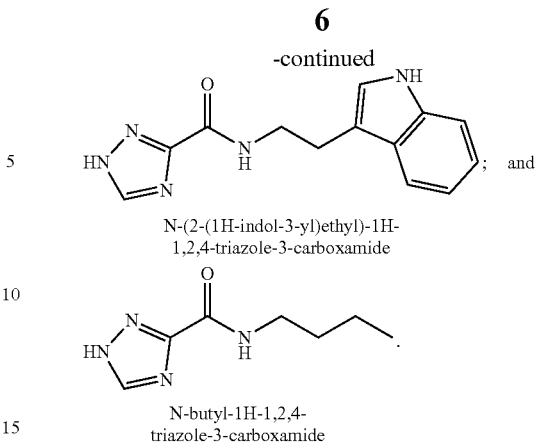

N-(2-(1H-indol-3-yl)ethyl)-1H-1,2,4-triazole-3-carboxamide

N-butyl-1H-1,2,4-triazole-3-carboxamide

In certain embodiments, the compound of Formula (I) is capable of binding DksA. In certain embodiments, the compound of Formula (I) inhibits DksA function. In other embodiments, the compound of Formula (I) inhibits the growth of gram-negative bacteria. In yet other embodiments, the compound of Formula (I) kills gram-negative bacteria.

In certain embodiments, compounds of the invention include any compound of Formula (I) having an MIC value lower than about 32 µg/ml capable of inhibiting rpsM in vitro transcription reactions with an $IC_{50}$ value of less than about 100 nM.

In certain embodiments, the compound of Formula (I) is formulated as part of a pharmaceutical composition, further comprising at least one pharmaceutically acceptable carrier. In certain embodiments, the pharmaceutical composition further comprises at least one additional therapeutic agent. In other embodiments, the at least one additional therapeutic agent is at least one antimicrobial agent. In yet other embodiments, the at least one additional therapeutic agent is at least one antibiotic or antibacterial agent.

The compounds of the invention may possess one or more stereocenters, and each stereocenter may exist independently in either the (R) or (S) configuration. In certain embodiments, compounds described herein are present in optically active or racemic forms. The compounds described herein encompass racemic, optically-active, regioisomeric and stereoisomeric forms, or combinations thereof that possess the therapeutically useful properties described herein. Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. In certain embodiments, a mixture of one or more isomer is utilized as the therapeutic compound described herein. In other embodiments, compounds described herein contain one or more chiral centers. These compounds are prepared by any means, including stereoselective synthesis, enantioselective synthesis and/or separation of a mixture of enantiomers and/or diastereoisomers. Resolution of compounds and isomers thereof is achieved by any means including, by way of non-limiting example, chemical processes, enzymatic processes, fractional crystallization, distillation, and chromatography.

The methods and formulations described herein include the use of N-oxides (if appropriate), crystalline forms (also known as polymorphs), solvates, amorphous phases, and/or pharmaceutically acceptable salts of compounds having the structure of any compound of the invention, as well as metabolites and active metabolites of these compounds having the same type of activity. Solvates include water, ether (e.g., tetrahydrofuran, methyl tert-butyl ether) or alcohol (e.g., ethanol) solvates, acetates and the like. In certain embodiments, the compounds described herein exist in solvated forms with pharmaceutically acceptable solvents such as water, and ethanol. In other embodiments, the compounds described herein exist in unsolvated form.

In certain embodiments, the compounds of the invention exist as tautomers. All tautomers are included within the scope of the compounds recited herein.

In certain embodiments, compounds described herein are prepared as prodrugs. A "prodrug" is an agent converted into the parent drug in vivo. In certain embodiments, upon in vivo administration, a prodrug is chemically converted to the biologically, pharmaceutically or therapeutically active form of the compound. In other embodiments, a prodrug is enzymatically metabolized by one or more steps or processes to the biologically, pharmaceutically or therapeutically active form of the compound.

In certain embodiments, sites on, for example, the aromatic ring portion of compounds of the invention are susceptible to various metabolic reactions. Incorporation of appropriate substituents on the aromatic ring structures may reduce, minimize or eliminate this metabolic pathway. In certain embodiments, the appropriate substituent to decrease or eliminate the susceptibility of the aromatic ring to metabolic reactions is, by way of example only, a deuterium, a halogen, or an alkyl group.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^2$H, $^3$H, $^{11}$C, $^{13}$C, $^{14}$C, $^{36}$Cl, $^{18}$F, $^{123}$I, $^{125}$I, $^{13}$N, $^{15}$N, $^{15}$O, $^{17}$O, $^{18}$O, $^{32}$P, and $^{35}$S. In certain embodiments, isotopically-labeled compounds are useful in drug and/or substrate tissue distribution studies. In other embodiments, substitution with heavier isotopes such as deuterium affords greater metabolic stability (for example, increased in vivo half-life or reduced dosage requirements). In yet other embodiments, substitution with positron emitting isotopes, such as $^{11}$C, $^{18}$F, $^{15}$O and $^{13}$N, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

In certain embodiments, the compounds described herein are labeled by other means, including, but not limited to, the use of chromophores or fluorescent moieties, bioluminescent labels, or chemiluminescent labels.

The compounds described herein may form salts with acids and/or bases, and such salts are included in the present invention. In certain embodiments, the salts are pharmaceutically acceptable salts. The term "salts" embraces addition salts of free acids and/or bases that are useful within the methods of the invention. The term "pharmaceutically acceptable salt" refers to salts that possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds useful within the methods of the invention.

Suitable pharmaceutically acceptable acid addition salts may be prepared from an inorganic acid or from an organic acid. Examples of inorganic acids include sulfate, hydrogen sulfate, hemisulfate, hydrochloric, hydrobromic, hydriodic, nitric, carbonic, sulfuric, and phosphoric acids (including hydrogen phosphate and dihydrogen phosphate). Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, O-hydroxybutyric, salicylic, galactaric, galacturonic acid, glycerophosphonic acids and saccharin (e.g., saccharinate, saccharate). Salts may be comprised of a fraction of one, one or more than one molar equivalent of acid or base with respect to any compound of the invention.

Suitable pharmaceutically acceptable base addition salts of compounds of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylene-diamine, chloroprocaine, choline, diethanolamine, ethylenediamine, meglumine (N-methylglucamine) and procaine. All of these salts may be prepared from the corresponding compound by reacting, for example, the appropriate acid or base with the compound.

Acid addition salts are generally formed by combining the target freebase with a salt former in a solvent, forming a solution, and collecting the salt as a solid. The molar ratio of salt former to free base may vary (e.g., 1:1, 2:1, 1:2, etc.). A ratio of 1:1 may be preferred. Solvents may include, but are not limited to methyl ethyl ketone, methyl isobutyl ketone, ethyl acetate, isopropyl acetate, water, heptane, methyl tert-butyl ether, cyclohexane, toluene, methanol, ethanol, n-propanol, isopropanol, n-butanol, 2-butanol, isoamyl alcohol, tetrahydrofuran and acetonitrile, and mixtures thereof.

Synthesis

The compounds described herein, and other related compounds having different substituents are synthesized using techniques and materials described herein and as described, for example, in Fieser & Fieser's Reagents for Organic Synthesis, Vol. 1-17 (John Wiley and Sons, 1991); Rodd's Chemistry of Carbon Compounds, Vol. 1-5 and Supplementals (Elsevier Science Publishers, 1989); Organic Reactions, Vol. 1-40 (John Wiley and Sons, 1991), Larock's Comprehensive Organic Transformations (VCH Publishers Inc., 1989), March, Advanced Organic Chemistry 4$^{th}$, Ed., (Wiley 1992); Carey & Sundberg, Advanced Organic Chemistry, 4$^{th}$ Ed., Vols. A and B (Plenum 2000, 2001), and Green & Wuts, Protective Groups in Organic Synthesis 3rd Ed., (Wiley 1999) (all of which are incorporated by reference for such disclosure). General methods for the preparation of compound as described herein are modified by the use of appropriate reagents and conditions, for the introduction of the various moieties found in the formula as provided herein.

Compounds described herein are synthesized using any suitable procedures starting from compounds that are available from commercial sources, or are prepared using procedures described herein. See, for example, Northen, et al., 2002, J. Chem. Soc., Perkin Trans. 1, 108-115; DOI: 10.1039/B102224P.

Methods

In another aspect, the invention provides a method of inhibiting growth and/or killing bacteria. In certain embodiments, the method comprises contacting a bacterium with a compound or composition of the invention.

In certain embodiments, the bacterium is gram-negative. In other embodiments, the bacterium is at least one selected from the group consisting of, but not necessarily limited to, Enterobacteriaceae family members, including *Klebsiella, E. coli, Proteus, Serratia, Salmonella, Yersinia,* and *Enterobacter, Pseudomonas aeruginosa, Neisseria gonorrhoeae, Chlamydia trachomatis, Acinetobacter* and *Stenotrophomonas*. In yet other embodiments, the bacterium has a DksA protein.

In certain embodiments, the invention provides a method of treating a bacterial infection in a subject in need thereof. In other embodiments, the method comprises administering to the subject a therapeutically effective amount of a pharmaceutical composition of the invention.

In certain embodiments, the bacterial infection is caused by a gram-negative bacterium. In other embodiments, the gram-negative bacterium is at least one selected from the group consisting of, but not necessarily limited to, Enterobacteriaceae family members, including *Klebsiella, E. coli, Proteus, Serratia, Salmonella, Yersinia,* and *Enterobacter, Pseudomonas aeruginosa, Neisseria gonorrhoeae, Chlamydia trachomatis, Acinetobacter* and *Stenotrophomonas*. In yet other embodiments, the bacterium has a DksA protein.

This invention also encompasses the use of compound or composition of this disclosure in the manufacture of a medicament for the treatment of a bacterial infection in a mammal, particularly a gram-negative bacterial infection.

Similarly, this invention provides a compound or composition of this disclosure for use in the treatment of a bacterial infection in a mammal, particularly a gram-negative bacterial infection.

In these methods, the subject is a mammal. In these methods, the subject may be a human.

Combination and Concurrent Therapies

In one embodiment, the compositions of the invention are useful in the methods of present invention when used concurrently with at least one additional compound useful for preventing and/or treating diseases and/or disorders contemplated herein.

In one embodiment, the compositions of the invention are useful in the methods of present invention in combination with at least one additional compound useful for preventing and/or treating diseases and/or disorders contemplated herein. In certain embodiments, the compositions of the invention are useful in combination with one or more antimicrobial, antibacterial or antibiotic compounds or compositions.

These additional compounds may comprise compounds of the present invention or other compounds, such as commercially available compounds, known to treat, prevent, or reduce the symptoms of diseases and/or disorders contemplated herein. In certain embodiments, the combination of at least one compound of the invention or a salt thereof, and at least one additional compound useful for preventing and/or treating diseases and/or disorders contemplated herein, has additive, complementary or synergistic effects in the prevention and/or treatment of diseases and/or disorders contemplated herein.

As used herein, combinations of two or more compounds may refer to a composition wherein the individual compounds are physically mixed or wherein the individual compounds are physically separated. A combination therapy encompasses administering the components separately to produce the desired additive, complementary or synergistic effects.

A synergistic effect may be calculated, for example, using suitable methods such as, for example, the Sigmoid-Emax equation (Holford & Scheiner, 19981, Clin. Pharmacokinet. 6: 429-453), the equation of Loewe additivity (Loewe & Muischnek, 1926, Arch. Exp. Pathol Pharmacol. 114: 313-326), the median-effect equation (Chou & Talalay, 1984, Adv. Enzyme Regul. 22: 27-55), and through the use of isobolograms (Tallarida & Raffa, 1996, Life Sci. 58: 23-28). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

Administration/Dosing

The regimen of administration may affect what constitutes an effective amount. The therapeutic formulations may be administered to the patient either prior to or after the onset of a bacterial infection. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient, preferably a mammal, more preferably a human, may be carried out using known procedures, at dosages and for periods of time effective to treat a bacterial infection in the patient. An effective amount of the therapeutic compound necessary to achieve a therapeutic effect may vary according to factors such as the activity of the particular compound employed; the time of administration; the rate of excretion of the compound; the duration of the treatment; other drugs, compounds or materials used in combination with the compound; the state of the disease or disorder, age, sex, weight, condition, general health and prior medical history of the patient being treated, and like factors well-known in the medical arts. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 0.01 mg/kg to 100 mg/kg of body weight/per day. One of ordinary skill in the art would be able to study the relevant factors and make the determination regarding the effective amount of the therapeutic compound without undue experimentation.

The compound may be administered to an animal as frequently as several times daily, or it may be administered less frequently, such as once a day, once a week, once every two weeks, once a month, or even less frequently, such as once every several months or even once a year or less. It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on. The frequency of the dose will be readily apparent to the skilled artisan and will depend upon any number of factors, such as, but not limited to, the type and severity of the disease being treated, the type and age of the animal, etc.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of a bacterial infection in a patient.

In certain embodiments, the compositions of the invention are administered to the patient in dosages that range from one to five times per day or more. In other embodiments, the compositions of the invention are administered to the patient in range of dosages that include, but are not limited to, once every day, every two days, every three days to once a week, and once every two weeks. It will be readily apparent to one skilled in the art that the frequency of administration of the various combination compositions of the invention will vary from subject to subject depending on many factors including, but not limited to, age, disease or disorder to be treated, gender, overall health, and other factors. Thus, the invention should not be construed to be limited to any particular dosage regime and the precise dosage and composition to be administered to any patient will be determined by the attending physician taking all other factors about the patient into account.

Compounds of the invention for administration may be in the range of from about 1 µg to about 7,500 mg, about 20 µg to about 7,000 mg, about 40 µg to about 6,500 mg, about 80 µg to about 6,000 mg, about 100 µg to about 5,500 mg, about 200 µg to about 5,000 mg, about 400 µg to about 4,000 mg, about 800 µg to about 3,000 mg, about 1 mg to about 2,500 mg, about 2 mg to about 2,000 mg, about 5 mg to about 1,000 mg, about 10 mg to about 750 mg, about 20 mg to about 600 mg, about 30 mg to about 500 mg, about 40 mg to about 400 mg, about 50 mg to about 300 mg, about 60 mg to about 250 mg, about 70 mg to about 200 mg, about 80 mg to about 150 mg, and any and all whole or partial increments there-in-between.

In some embodiments, the dose of a compound of the invention is from about 0.5 µg and about 5,000 mg. In some embodiments, a dose of a compound of the invention used in compositions described herein is less than about 5,000 mg, or less than about 4,000 mg, or less than about 3,000 mg, or less than about 2,000 mg, or less than about 1,000 mg, or less than about 800 mg, or less than about 600 mg, or less than about 500 mg, or less than about 200 mg, or less than about 50 mg. Similarly, in some embodiments, a dose of a second compound as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In certain embodiments, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of bacterial infection in a patient.

The term "container" includes any receptacle for holding the pharmaceutical composition or for managing stability or water uptake. For example, in certain embodiments, the container is the packaging that contains the pharmaceutical composition, such as liquid (solution and suspension), semi-solid, lyophilized solid, solution and powder or lyophilized formulation present in dual chambers. In other embodiments, the container is not the packaging that contains the pharmaceutical composition, i.e., the container is a receptacle, such as a box or vial that contains the packaged pharmaceutical composition or unpackaged pharmaceutical composition and the instructions for use of the pharmaceutical composition. Moreover, packaging techniques are well known in the art. It should be understood that the instructions for use of the pharmaceutical composition may be contained on the packaging containing the pharmaceutical composition, and as such the instructions form an increased functional relationship to the packaged product. However, it should be understood that the instructions may contain information pertaining to the compound's ability to perform its intended function, e.g., treating, preventing, or reducing a bacterial infection in a patient.

Administration

Routes of administration of any of the compositions of the invention include inhalational, oral, nasal, rectal, parenteral, sublingual, transdermal, transmucosal (e.g., sublingual, lingual, (trans)buccal, (trans)urethral, vaginal (e.g., trans- and perivaginally), (intra)nasal, and (trans)rectal), intravesical, intrapulmonary, intraduodenal, intragastrical, intrathecal, epidural, intrapleural, intraperitoneal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, emulsions, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

Parenteral Administration

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intravenous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multidose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

Topical Administration

An obstacle for topical administration of pharmaceuticals is the stratum corneum layer of the epidermis. The stratum corneum is a highly resistant layer comprised of protein, cholesterol, sphingolipids, free fatty acids and various other lipids, and includes cornified and living cells. One of the factors that limit the penetration rate (flux) of a compound through the stratum corneum is the amount of the active substance that can be loaded or applied onto the skin surface. The greater the amount of active substance which is applied per unit of area of the skin, the greater the concentration gradient between the skin surface and the lower layers of the skin, and in turn the greater the diffusion force of the active substance through the skin. Therefore, a formulation containing a greater concentration of the active substance is more likely to result in penetration of the active substance through the skin, and more of it, and at a more consistent rate, than a formulation having a lesser concentration, all other things being equal.

Formulations suitable for topical administration include, but are not limited to, liquid or semi-liquid preparations such as liniments, lotions, oil-in-water or water-in-oil emulsions such as creams, ointments or pastes, and solutions or suspensions. Topically administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

Enhancers of permeation may be used. These materials increase the rate of penetration of drugs across the skin. Typical enhancers in the art include ethanol, glycerol monolaurate, PGML (polyethylene glycol monolaurate), dimethylsulfoxide, and the like. Other enhancers include oleic acid, oleyl alcohol, ethoxydiglycol, laurocapram, alkanecarboxylic acids, dimethylsulfoxide, polar lipids, or N-methyl-2-pyrrolidone. One acceptable vehicle for topical delivery of some of the compositions of the invention may contain liposomes.

Buccal Administration

A pharmaceutical composition of the invention may be prepared, packaged, or sold in a formulation suitable for buccal administration. Such formulations may, for example, be in the form of tablets or lozenges made using conventional methods, and may contain, for example, 0.1 to 20% (w/w) of the active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein. The examples of formulations described herein are not exhaustive and it is understood that the invention includes additional modifications of these and other formulations not described herein, but known to those of skill in the art.

Rectal Administration

A pharmaceutical composition of the invention may be prepared, packaged, or sold in a formulation suitable for rectal administration. Such a composition may be in the form of, for example, a suppository, a retention enema preparation, and a solution for rectal or colonic irrigation.

Suppository formulations may be made by combining the active ingredient with a non-irritating pharmaceutically acceptable excipient which is solid at ordinary room temperature (i.e., about 20° C.) and which is liquid at the rectal temperature of the subject (i.e., about 37° C. in a healthy human). Suitable pharmaceutically acceptable excipients include, but are not limited to, cocoa butter, polyethylene glycols, and various glycerides. Suppository formulations may further comprise various additional ingredients including, but not limited to, antioxidants, and preservatives.

Retention enema preparations or solutions for rectal or colonic irrigation may be made by combining the active ingredient with a pharmaceutically acceptable liquid carrier. As is well known in the art, enema preparations may be administered using, and may be packaged within, a delivery device adapted to the rectal anatomy of the subject. Enema preparations may further comprise various additional ingredients including, but not limited to, antioxidants, and preservatives.

Additional Administration Forms

Additional dosage forms of this invention include dosage forms as described in U.S. Pat. Nos. 6,340,475, 6,488,962, 6,451,808, 5,972,389, 5,582,837, and 5,007,790. Additional dosage forms of this invention also include dosage forms as described in U.S. Patent Applications Nos. 20030147952, 20030104062, 20030104053, 20030044466, 20030039688, and 20020051820. Additional dosage forms of this invention also include dosage forms as described in PCT Applications Nos. WO 03/35041, WO 03/35040, WO 03/35029, WO 03/35177, WO 03/35039, WO 02/96404, WO 02/32416, WO 01/97783, WO 01/56544, WO 01/32217, WO 98/55107, WO 98/11879, WO 97/47285, WO 93/18755, and WO 90/11757.

Definitions

As used herein, each of the following terms has the meaning associated with it in this section.

Unless defined otherwise, all technical and scientific terms used herein generally have the same meaning as commonly understood by one of ordinary skill in the art to which this invention belongs. Generally, the nomenclature used herein and the laboratory procedures in animal pharmacology, pharmaceutical science, separation science and organic chemistry are those well-known and commonly employed in the art. It should be understood that the order of steps or order for performing certain actions is immaterial, so long as the present teachings remain operable. Moreover, two or more steps or actions can be conducted simultaneously or not.

As used herein, the articles "a" and "an" refer to one or to more than one (i.e., to at least one) of the grammatical object of the article. By way of example, "an element" means one element or more than one element.

As used herein, the term "alkoxy" employed alone or in combination with other terms means, unless otherwise stated, an alkyl group having the designated number of carbon atoms, as defined elsewhere herein, connected to the rest of the molecule via an oxygen atom, such as, for example, methoxy, ethoxy, 1-propoxy, 2-propoxy (or isopropoxy) and the higher homologs and isomers. A specific example is $(C_1-C_3)$alkoxy, such as, but not limited to, ethoxy and methoxy.

As used herein, the term "alkyl" by itself or as part of another substituent means, unless otherwise stated, a straight or branched chain hydrocarbon having the number of carbon atoms designated (i.e., $C_1-C_{10}$ means one to ten carbon atoms) and includes straight, branched chain, or cyclic substituent groups. Examples include methyl, ethyl, propyl, isopropyl, butyl, isobutyl, tert-butyl, pentyl, neopentyl, hexyl, and cyclopropylmethyl. A specific embodiment is $(C_1-C_6)$alkyl, such as, but not limited to, ethyl, methyl, isopropyl, isobutyl, n-pentyl, n-hexyl and cyclopropylmethyl.

As used herein, the term "alkylene" by itself or as part of another substituent means, unless otherwise stated, a straight or branched hydrocarbon group having the number of carbon atoms designated (i.e., $C_1-C_{10}$ means one to ten carbon atoms) and includes straight, branched chain, or cyclic substituent groups, wherein the group has two open valencies. Examples include methylene, 1,2-ethylene, 1,1-ethylene, 1,1-propylene, 1,2-propylene and 1,3-propylene.

As used herein, the term "aromatic" refers to a carbocycle or heterocycle with one or more polyunsaturated rings and having aromatic character, i.e. having (4n+2) delocalized □ (pi) electrons, where n is an integer.

As used herein, the term "aryl," employed alone or in combination with other terms, means, unless otherwise stated, a carbocyclic aromatic system containing one or more rings (typically one, two or three rings) wherein such rings may be attached together in a pendent manner, such as a biphenyl, or may be fused, such as naphthalene. Examples include phenyl, anthracyl, and naphthyl.

As used herein, the term "aryl-$(C_1-C_6)$alkyl" refers to a functional group wherein a one to six carbon alkanediyl chain is attached to an aryl group, e.g., —$CH_2CH_2$-phenyl or —$CH_2$-phenyl (or benzyl). Specific examples are aryl-$CH_2$— and aryl-$CH(CH_3)$—. The term "substituted aryl-$(C_1-C_6)$alkyl" refers to an aryl-$(C_1-C_6)$alkyl functional group in which the aryl group is substituted. A specific example is substituted aryl($CH_2$)—. Similarly, the term "heteroaryl-$(C_1-C_6)$alkyl" refers to a functional group wherein a one to three carbon alkanediyl chain is attached to a heteroaryl group, e.g., —$CH_2CH_2$-pyridyl. A specific example is heteroaryl-($CH_2$)—. The term "substituted heteroaryl-$(C_1-C_6)$alkyl" refers to a heteroaryl-$(C_1-C_6)$alkyl functional group in which the heteroaryl group is substituted. A specific example is substituted heteroaryl-($CH_2$)—.

As used herein, the term "cycloalkyl" by itself or as part of another substituent refers to, unless otherwise stated, a cyclic chain hydrocarbon having the number of carbon atoms designated (i.e., $C_3-C_6$ refers to a cyclic group comprising a ring group consisting of three to six carbon atoms) and includes straight, branched chain or cyclic substituent groups. Examples of $(C_3-C_6)$cycloalkyl groups are cyclopropyl, cyclobutyl, cyclopentyl and cyclohexyl. Cycloalkyl rings can be optionally substituted. Non-limiting examples of cycloalkyl groups include: cyclopropyl, 2-methyl-cyclopropyl, cyclopropenyl, cyclobutyl, 2,3-dihydroxycyclobutyl, cyclobutenyl, cyclopentyl, cyclopentenyl, cyclopentadienyl, cyclohexyl, cyclohexenyl, cycloheptyl, cyclooctanyl, decalinyl, 2,5-dimethylcyclopentyl, 3,5-dichlorocyclohexyl, 4-hydroxycyclohexyl, 3,3,5-trimethylcyclohex-1-yl, octahydropentalenyl, octahydro-1H-indenyl, 3a,4,5,6,7,7a-hexahydro-3H-inden-4-yl, decahydroazulenyl; bicyclo[6.2.0]decanyl, decahydronaphthalenyl, and dodecahydro-1H-fluorenyl. The term "cycloalkyl" also includes bicyclic hydrocarbon rings, non-limiting examples of which include, bicyclo-[2.1.1]hexanyl, bicyclo[2.2.1]

heptanyl, bicyclo[3.1.1]heptanyl, 1,3-dimethyl[2.2.1]heptan-2-yl, bicyclo[2.2.2]octanyl, and bicyclo[3.3.3]undecanyl.

As used herein, the term "halide" refers to a halogen atom bearing a negative charge. The halide anions are fluoride ($F^-$), chloride ($Cl^-$), bromide ($Br^-$), and iodide ($I^-$).

As used herein, the term "halo" or "halogen" alone or as part of another substituent refers to, unless otherwise stated, a fluorine, chlorine, bromine, or iodine atom.

As used herein, the language "pharmaceutically acceptable salt" refers to a salt of the administered compound prepared from pharmaceutically acceptable non-toxic acids and/or bases, including inorganic acids, inorganic bases, organic acids, inorganic bases, solvates (including hydrates) and clathrates thereof.

As used herein, the term "heteroalkyl" by itself or in combination with another term refers to, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—$CH_2$—$CH_2$—$CH_3$, —$CH_2$—$CH_2$—$CH_2$—OH, —$CH_2$—$CH_2$—NH—$CH_3$, —$CH_2$—S—$CH_2$—$CH_3$, and —$CH_2CH_2$—S(=O)—$CH_3$. Up to two heteroatoms may be consecutive, such as, for example, —$CH_2$—NH—$OCH_3$, or —$CH_2$—$CH_2$—S—S—$CH_3$.

As used herein, the term "heterocycle" or "heterocyclyl" or "heterocyclic" by itself or as part of another substituent refers to, unless otherwise stated, an unsubstituted or substituted, stable, mono- or multi-cyclic heterocyclic ring system that consists of carbon atoms and at least one heteroatom selected from the group consisting of N, O, and S, and wherein the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In certain embodiments, the heterocycle is a heteroaryl.

As used herein, the term "heteroaryl" or "heteroaromatic" refers to a heterocycle having aromatic character. A polycyclic heteroaryl may include one or more rings that are partially saturated. Examples include tetrahydroquinoline and 2,3-dihydrobenzofuryl.

Examples of non-aromatic heterocycles include monocyclic groups such as aziridine, oxirane, thiirane, azetidine, oxetane, thietane, pyrrolidine, pyrroline, imidazoline, pyrazolidine, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin and hexamethyleneoxide.

Examples of heteroaryl groups include pyridyl, pyrazinyl, pyrimidinyl (such as, but not limited to, 2- and 4-pyrimidinyl), pyridazinyl, thienyl, furyl, pyrrolyl, imidazolyl, thiazolyl, oxazolyl, pyrazolyl, isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles include indolyl (such as, but not limited to: 3-, 4-, 5-, 6-, and 7-indolyl), indolinyl, quinolyl, tetrahydroquinolyl, isoquinolyl (such as, but not limited to, 1- and 5-isoquinolyl), 1,2,3,4-tetrahydroisoquinolyl, cinnolinyl, quinoxalinyl (such as, but not limited to, 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (such as, but not limited to, 3-, 4-, 5-, 6- and 7-benzofuryl), 2,3-dihydrobenzofuryl, 1,2-benzisoxazolyl, benzothienyl (such as, but not limited to, 3-, 4-, 5-, 6-, and 7-benzothienyl), benzoxazolyl, benzothiazolyl (such as, but not limited to, 2-benzothiazolyl and 5-benzothiazolyl), purinyl, benzimidazolyl, benztriazolyl, thioxanthinyl, carbazolyl, carbolinyl, acridinyl, pyrrolizidinyl, and quinolizidinyl.

The aforementioned listing of heterocyclic and heteroaryl moieties is intended to be representative and not limiting.

As used herein, the term "substituted" refers to that an atom or group of atoms has replaced hydrogen as the substituent attached to another group.

As used herein, the term "substituted alkyl" or "substituted cycloalkyl" refers to alkyl or cycloalkyl, as defined elsewhere herein, substituted by one, two or three substituents independently selected from the group consisting of halogen, —OH, alkoxy, tetrahydro-2-H-pyranyl, —$NH_2$, —NH($C_1$-$C_6$ alkyl), —N($C_1$-$C_6$ alkyl)$_2$, 1-methyl-imidazol-2-yl, pyridin-2-yl, pyridin-3-yl, pyridin-4-yl, —C(=O)OH, —C(=O)O($C_1$-$C_6$)alkyl, trifluoromethyl, —C≡N, —C(=O)$NH_2$, —C(=O)NH($C_1$-$C_6$)alkyl, —C(=O)N(($C_1$-$C_6$)alkyl)$_2$, —$SO_2NH_2$, —$SO_2$NH($C_1$-$C_6$ alkyl), —$SO_2$N($C_1$-$C_6$ alkyl)$_2$, —C(=NH)$NH_2$, and —$NO_2$, in certain embodiments containing one or two substituents independently selected from halogen, —OH, alkoxy, —$NH_2$, trifluoromethyl, —N($CH_3$)$_2$, and —C(=O)OH, in certain embodiments independently selected from halogen, alkoxy and —OH. Examples of substituted alkyls include, but are not limited to, 2,2-difluoropropyl, 2-carboxycyclopentyl and 3-chloropropyl.

For aryl, aryl-($C_1$-$C_3$)alkyl and heterocyclyl groups, the term "substituted" as applied to the rings of these groups refers to any level of substitution, namely mono-, di-, tri-, tetra-, or penta-substitution, where such substitution is permitted. The substituents are independently selected, and substitution may be at any chemically accessible position. In certain embodiments, the substituents vary in number between one and four. In other embodiments, the substituents vary in number between one and three. In yet another embodiments, the substituents vary in number between one and two. In yet other embodiments, the substituents are independently selected from the group consisting of $C_1$-$C_6$ alkyl, —OH, $C_1$-$C_6$ alkoxy, halo, amino, acetamido and nitro. As used herein, where a substituent is an alkyl or alkoxy group, the carbon chain may be branched, straight or cyclic.

Unless otherwise noted, when two substituents are taken together to form a ring having a specified number of ring atoms (e.g., $R^2$ and $R^3$ taken together with the nitrogen to which they are attached to form a ring having from 3 to 7 ring members), the ring can have carbon atoms and optionally one or more (e.g., 1 to 3) additional heteroatoms independently selected from nitrogen, oxygen, or sulfur. The ring can be saturated or partially saturated, and can be optionally substituted.

Whenever a term or either of their prefix roots appear in a name of a substituent the name is to be interpreted as including those limitations provided herein. For example, whenever the term "alkyl" or "aryl" or either of their prefix roots appear in a name of a substituent (e.g., arylalkyl, alkylamino) the name is to be interpreted as including those limitations given elsewhere herein for "alkyl" and "aryl" respectively.

In certain embodiments, substituents of compounds are disclosed in groups or in ranges. It is specifically intended that the description include each and every individual subcombination of the members of such groups and ranges. For example, the term "$C_{1-6}$ alkyl" is specifically intended to individually disclose $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$ alkyl.

As used herein, the term "bacteria" means a large domain of prokaryotic microorganisms. Typically a few micrometres in length, bacteria have a wide range of shapes, ranging from spheres to rods and spirals. There are broadly speaking two different types of cell wall in bacteria, called Gram-positive and Gram-negative. Gram-positive bacteria possess a thick cell wall containing many layers of peptidoglycan and teichoic acids. In contrast, Gram-negative bacteria have a relatively thin cell wall consisting of a few layers of peptidoglycan surrounded by a second lipid membrane containing lipopolysaccharides and lipoproteins.

As used herein, the term "composition" or "pharmaceutical composition" refers to a mixture of at least one compound useful within the invention with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, nasal, pulmonary and topical administration.

A "disease" as used herein is a state of health of an animal wherein the animal cannot maintain homeostasis, and wherein if the disease is not ameliorated then the animal's health continues to deteriorate.

A "disorder" as used herein in an animal is a state of health in which the animal is able to maintain homeostasis, but in which the animal's state of health is less favorable than it would be in the absence of the disorder. Left untreated, a disorder does not necessarily cause a further decrease in the animal's state of health.

The terms "patient," "subject" or "individual" are used interchangeably herein, and refer to any animal, or cells thereof whether in vitro or in situ, amenable to the methods described herein. In a non-limiting embodiment, the patient, subject or individual is a human.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that can be included in the pharmaceutical compositions used in the practice of the invention are known in the art and described, for example in Remington's Pharmaceutical Sciences (Genaro, Ed., Mack Publishing Co., 1985, Easton, PA), which is incorporated herein by reference.

As used herein, the language "pharmaceutically acceptable salt" refers to a salt of the administered compounds prepared from pharmaceutically acceptable non-toxic acids, including inorganic acids, organic acids, solvates, hydrates, or clathrates thereof.

The term "prevent," "preventing" or "prevention," as used herein, means avoiding or delaying the onset of symptoms associated with a disease or condition in a subject that has not developed such symptoms at the time the administering of an agent or compound commences.

A "therapeutic" treatment is a treatment administered to a subject who exhibits signs of pathology, for the purpose of diminishing or eliminating those signs.

As used herein, the term "therapeutically effective amount" refers to an amount that is sufficient or effective to prevent or treat (delay or prevent the onset of, prevent the progression of, inhibit, decrease or reverse) a disease or condition described or contemplated herein, including alleviating symptoms of such disease or condition.

As used herein, the term "treatment" or "treating" is defined as the application or administration of a therapeutic agent, i.e., a compound of the invention (alone or in combination with another pharmaceutical agent), to a patient, or application or administration of a therapeutic agent to an isolated tissue or cell line from a patient (e.g., for diagnosis or ex vivo applications), who has a condition contemplated herein, a symptom of a condition contemplated herein or the potential to develop a condition contemplated herein, with the purpose to cure, heal, alleviate, relieve, alter, remedy, ameliorate, improve or affect a condition contemplated herein, the symptoms of a condition contemplated herein or the potential to develop a condition contemplated herein. Such treatments may be specifically tailored or modified, based on knowledge obtained from the field of pharmacogenomics.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual and partial numbers within that range, for example, 1, 2, 2.7, 3, 4, 5, 5.3, and 6. This applies regardless of the breadth of the range.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that, wherever values and ranges are provided herein, the description in range format is merely for convenience and brevity and should not be construed as an inflexible limitation on the scope of the invention. Accordingly, all values and ranges encompassed by these values and ranges are meant to be encompassed within the scope of the present invention. Moreover, all values that fall within these ranges, as well as the upper or lower limits of a range of values, are also contemplated by the present application. The description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

The following examples further illustrate aspects of the invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Materials and Methods

The $^1$H and $^{13}$C NMR spectra were recorded using a 400 MHz Bruker NMR, Avance III 400. The chemical shifts are reported in ppm. An Applied Biosystems Sciex 4000 (Applied Biosystems; Foster City, CA) was equipped with a Shimadzu HPLC (Shimadzu Scientific Instruments, Inc.; Columbia, MD) and Leap auto-sampler (LEAP Technologies; Carrboro, NC) was used to perform the LC/MS-MS. Nitrogen gas was procured from AirGas (Denver, CO). Reactions were monitored via silica gel IB2-F thin layer chromatography (TLC) plates from J.T. Baker (Phillipsburg, NJ). Silica Gel 60 Å 40-63 µm was purchased from Sorbent Technologies (Norcross, GA).

Anhydrous DMF (dimethylforamide), HPLC grade water, acetonitrile (ACN), dimethyl sulfoxide (DMSO), ethyl acetate (EtOAc), hexanes, methanol (MeOH), methylene chloride (DCM), anhydrous sodium sulfate ($Na_2SO_4$), ammonium acetate ($NH_4OAC$) and formic acid were purchased from Fisher Scientific (Pittsburgh, PA). 1H-1,2,4-Triazole-3-carboxylic acid, DMSO-$d_6$, 3,4-dimethoxyaniline, 1-hydroxybenzotriazole monohydrate, EDC (N-(3-Dimethylaminopropyl)-N'-ethylcarbodiimide), N-methylmorpholine, (3,4-dimethoxybenzyl)amine, (2,3-dimethoxybenzyl)amine, (4-methoxyphenyl)methanamine, 3-(trifluoromethoxy) aniline, piperonylamine, 4-(trifluoromethoxy)benzylamine, 3-methoxybenzylamine, 4-(trifluoromethoxy)benzylamine, 3-(trifluoromethoxy)benzylamine, 4-(trifluoromethoxy) benzylamine, 3-(trifluoromethoxy)benzylamine, 4-methoxy-3-(trifluoromethyl)benzylamine, 4-methoxy-3-(trifluoromethyl)benzylamine, 4-(trifluoromethyl)aniline, butan-1-amine, 4-(tert-butyl)aniline, 4-(trifluoromethyl)aniline, 3,5-dichloroaniline, 3-phenylpropan-1-amine, 4-phenylbutan-1-amine, (R)-(+)-α-methyl benzyl amine, (S)-(α)-methyl benzyl amine, 2-(1H-indol-3-yl)ethanamine, 2-phenylethanamine, 2-(4-methoxyphenyl)ethanamine, (R)-(+)-4-Methoxy-α-methylbenzylamine were procured from Sigma-Aldrich Chemical Company (St. Louis, MO)

Procedures for In Vitro Transcription (IVT) Assays

To measure the potency of a compound in inhibition of DksA biological function, rpsMtranscripts in vitro was determined by non-radioactive in vitro transcription reactions with qPCR analysis with divergent compounds.

Briefly, 5 nM pTIM-rpsMplasmid was mixed with 0.1-100 nM of compounds in 10 µl reaction buffer (40 mM HEPES [pH 7.4], 2 mM MgCl$_2$, 60 mM potassium glutamate, 0.05% NP-40, 200 µM ATP, 200 µM GTP, 200 µM CTP, 200 µM UTP, and 5 nM E. coli RNA polymerase holoenzyme (NEB, Ipswich, MA) with 5 µM DksA. The in vitro transcription was carried out at 37° C. for 10 min, and then terminated at 70° C. for 10 min. To remove template DNA after treated with DNaseI, DNA-free DNA Removal kit (ThermoFisher) was used according to manufacturer's direction. The resulting materials were used as templates to generate cDNA with 100 U MMLV reverse transcriptase (Promega), 0.45 µM gene specific primer, and 20 U RNase inhibitor (Promega). The amount of cDNA synthesized for 1 h at 42° C. was quantified by real-time PCR (qRT-PCR). The copy number of specific transcripts was calculated to the standard curve generated with known gene copy concentrations. The IC50 is the concentration at which the curve passes through the 50% inhibition level. Standard deviation was calculated from 3 independent experiments.

Procedures for Disk Diffusion Assays

*Salmonella* was grown overnight in LB broth at 37° C. with shaking. The bacterial cultures were diluted by 1:1000 with PBS. 100 µl of the diluted samples were transferred into E-salts glucose agar. The bacteria were spread on the surface of the agar. Two discs (BBL blank paper discs 6 mm) were placed per/plate, and 10 µl of 10 mM or 100 mM stock compound were added to the discs. The plates were incubated at 37° C. overnight. The diameter of inhibition was expressed in mm.

In Silico Modeling

Structural investigation of DksA showed that there is an area of negatively charged pocket in the coiled-coil domain, consisting of eight acidic residues: Asp[64], Asp[65], Asp[71], Asp[74], Glu[79], Gu[80], Glu[81], and Glu[85]. DOCK (Kuntz, et al., J. Mol. Biol. 161 (2), 269-288) was used to search several databases containing more than a hundred thousand small molecule drug candidates. Over 400 potential drug molecules matched the shapes and charges of acidic pocket at the tip of DksA. A panel of 40 compounds was selected from the top hits based on free energy binding scores. The surface complementarity between DksA and the compounds were inspected using a 3D modeling program. The interactions between these small molecules and DksA were further refined using energy minimization. These compounds were tested for their ability to interfere with DksA. The compound 916 (N-(3,4-dimethoxyphenyl)-1H-1,2,4-triazole-3-carboxamide, prior art) showed the best in vitro efficacy in preventing DksA-mediated repression of rpsM transcription. Modeling of compound 916 showed that the triazole ring was in van der Walls contact with Glu[80], Glu[81], and also interacted through several hydrogen bonds. The phenol moiety was tucked into the cavity between Asp[65] and Glu[79]. To improve the efficacy of candidate inhibitory drugs, compound 916 served as the basis for the development of additional compounds to screen. Based on free energy binding scores and molecular complementarity, several derivatives were identified with potentially greater binding affinity towards DksA.

Example 1: Synthesis of Selected Compounds

TABLE 1

Compounds Synthesized

| Cmpd. ID | Structure | Cmpd. Name | Molecular weight |
|---|---|---|---|
| 1 | 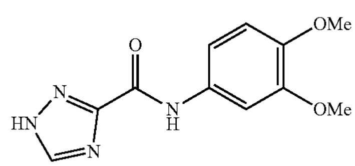 [SMILES: COc1ccc(NC(=O)c2nc[nH]n2)cc1OC] | N-(3,4-dimethoxyphenyl)-1H-1,2,4-triazole-3-carboxamide | 248.24 |
| 2 | 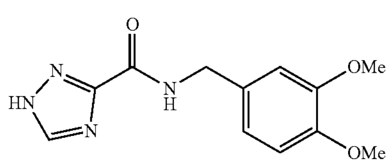 [SMILES: COc1ccc(CNC(=O)c2nc[nH]n2)cc1OC] | N-(3,4-dimethoxybenzyl)-1H-1,2,4-triazole-3-carboxamide | 262.26 |
| 3 | 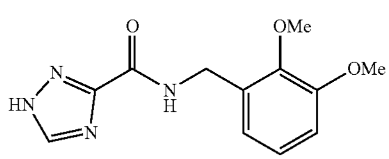 [SMILES: COc1cccc(CNC(=O)c2nc[nH]n2)c1OC] | N-(2,3-dimethoxybenzyl)-1H-1,2,4-triazole-3-carboxamide | 262.26 |
| 4 | 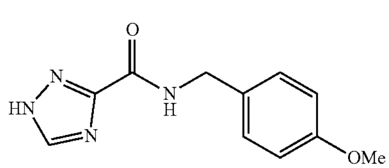 [SMILES: COc1ccc(CNC(=O)c2nc[nH]n2)cc1] | N-(4-methoxybenzyl)-1H-1,2,4-triazole-3-carboxamide | 232.24 |

TABLE 1-continued

Compounds Synthesized

| Cmpd. ID | Structure | Cmpd. Name | Molecular weight |
|---|---|---|---|
| 5 | 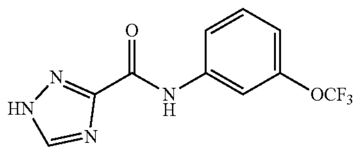 [SMILES: O=C(Nc1cccc(OC(F)(F)F)c1)c1nc[nH]n1] | N-(3-(trifluoromethoxy)phenyl)-1H-1,2,4-triazole-3-carboxamide | 272.18 |
| 6 | 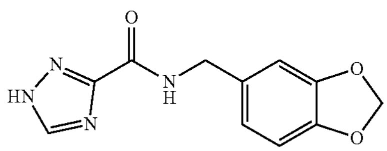 [SMILES: O=C(NCc1ccc2c(c1)OCO2)c1nc[nH]n1] | N-(benzo[d][1,3]dioxol-5-ylmethyl)-1H-1,2,4-triazole-3-carboxamide | 246.22 |
| 7 | 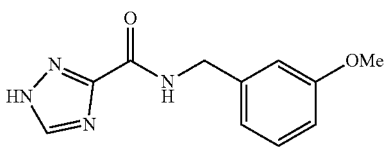 [SMILES: COc1cccc(CNC(=O)c2nc[nH]n2)c1] | N-(3-methoxybenzyl)-1H-1,2,4-triazole-3-carboxamide | 232.24 |
| 8 | 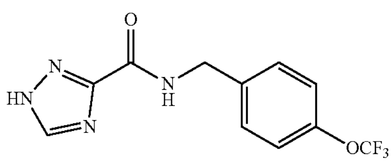 [SMILES: O=C(NCc1ccc(OC(F)(F)F)cc1)c1nc[nH]n1] | N-(4-(trifluoromethoxy)benzyl)-1H-1,2,4-triazole-3-carboxamide | 286.21 |
| 9 | 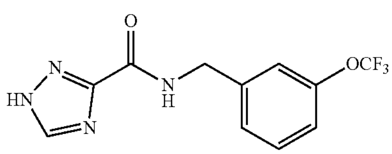 [SMILES: O=C(NCc1cccc(OC(F)(F)F)c1)c1nc[nH]n1] | N-(3-(trifluoromethoxy)benzyl)-1H-1,2,4-triazole-3-carboxamide | 286.21 |
| 10 | 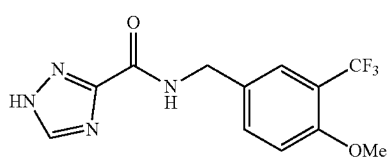 [SMILES: COc1ccc(CNC(=O)c2nc[nH]n2)cc1C(F)(F)F] | N-(4-methoxy-3-(trifluoromethyl)benzyl)-1H-1,2,4-triazole-3-carboxamide | 300.24 |
| 11 | 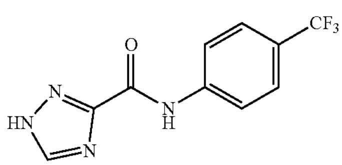 [SMILES: O=C(Nc1ccc(C(F)(F)F)cc1)c1nc[nH]n1] | N-(4-(trifluoromethyl)phenyl)-1H-1,2,4-triazole-3-carboxamide | 256.18 |
| 12 | 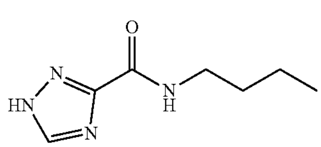 | N-butyl-1H-1,2,4-triazole-3-carboxamide | 168.20 |
| 13 | 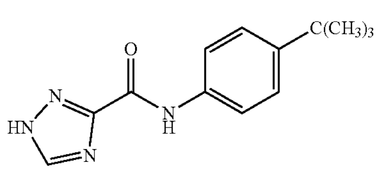 [SMILES: CC(C)(C)c1ccc(NC(=O)c2nc[nH]n2)cc1] | N-(4-(tert-butyl)phenyl)-1H-1,2,4-triazole-3-carboxamide | 244.29 |

TABLE 1-continued

Compounds Synthesized

| Cmpd. ID | Structure | Cmpd. Name | Molecular weight |
|---|---|---|---|
| 14 | 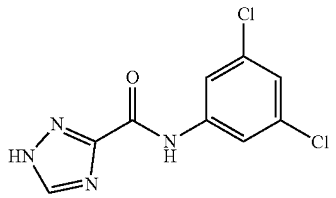 [SMILES: O=C(Nc1cc(Cl)cc(Cl)c1)c1nc[nH]n1] | N-(3,5-dichlorophenyl)-1H-1,2,4-triazole-3-carboxamide | 257.08 |
| 15 | 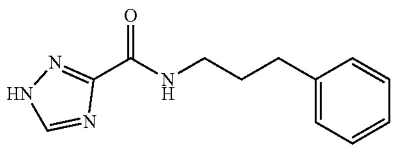 [SMILES: O=C(NCCCc1ccccc1)c1nc[nH]n1] | N-(3-phenylpropyl)-1H-1,2,4-triazole-3-carboxamide | 230.27 |
| 16 | 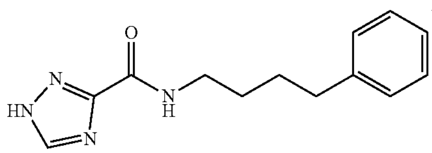 | N-(4-phenylbutyl)-1H-1,2,4-triazole-3-carboxamide | 244.29 |
| 17 | 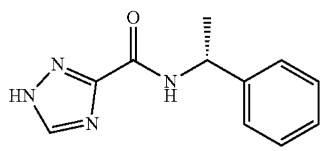 [SMILES: C[C@@H](NC(=O)c1nc[nH]n1)c1ccccc1] | (R)-N-(1-phenylethyl)-1H-1,2,4-triazole-3-carboxamide | 216.24 |
| 18 | 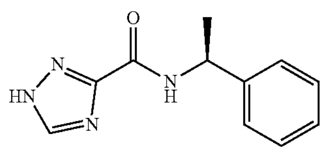 [SMILES: C[C@H](NC(=O)c1nc[nH]n1)c1ccccc1] | (S)-N-(1-phenylethyl)-1H-1,2,4-triazole-3-carboxamide | 216.24 |
| 19 | 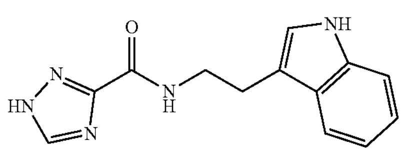 [SMILES: O=C(NCCc1c[nH]c2ccccc12)c1nc[nH]n1] | N-(2-(1H-indol-3-yl)ethyl)-1H-1,2,4-triazole-3-carboxamide | 255.28 |
| 20 | 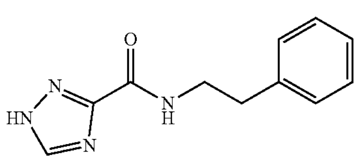 [SMILES: O=C(NCCc1ccccc1)c1nc[nH]n1] | N-phenethyl-1H-1,2,4-triazole-3-carboxamide | 216.24 |
| 21 | 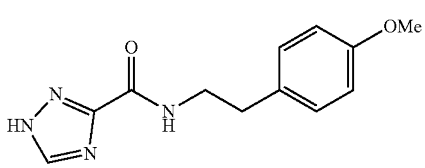 [SMILES: COc1ccc(CCNC(=O)c2nc[nH]n2)cc1] | N-(4-methoxyphenethyl)-1H-1,2,4-triazole-3-carboxamide | 246.27 |
| 22 | 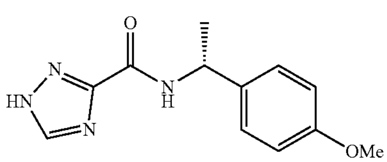 [SMILES: COc1ccc([C@@H](C)NC(=O)c2nc[nH]n2)cc1] | (R)-N-(1-(4-methoxyphenyl)ethyl)-1H-1,2,4-triazole-3-carboxamide | 246.27 |

Synthesis of 1

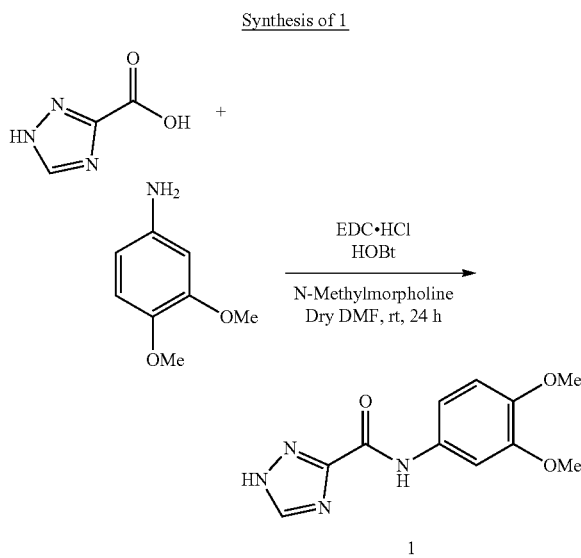

To a reaction of 1H-1,2,4-triazole-3-carboxylic acid (226 mg, 2.0 mmol) and 3,4-dimethoxyaniline (322 mg, 2.1 mmol) in dry DMF (10 mL) was added 1-hydroxybenzotriazole monohydrate (337 mg, 2.2 mmol) and EDC (N-(3-dimethylaminopropyl)-N'-ethylcarbodiimide) (422 mg, 2.2 mmol) followed by N-methylmorpholine (0.88 mL, 8.0 mmol via syringe). The mixture was stirred at room temperature under nitrogen and the solids were gradually dissolved. The contents were stirred at room temperature for 24.0 h, and then slowly diluted into ice cold water and extracted with DCM (50 mL×2). The DCM phase was washed with cold water (100 mL×2). The DCM phase was dried over anhydrous $Na_2SO_4$, filtered and concentrated under reduced pressure and then chromatographed on silica gel using EtOAc as eluent to get the desired amide 1 (60 mg, 12% yield) as a light brown solid. $^1$H-NMR (400 MHz, DMSO-$d_6$): δ14.79 (br s, 1H), 10.34 (br s, 1H), 8.58 (br s, 1H), 7.55-7.44 (m, 2H), 6.94-6.93 (m, 1H), 3.76-3.74 (m, 6H) ppm. MH+=263.2 m/z.

Synthesis of 2

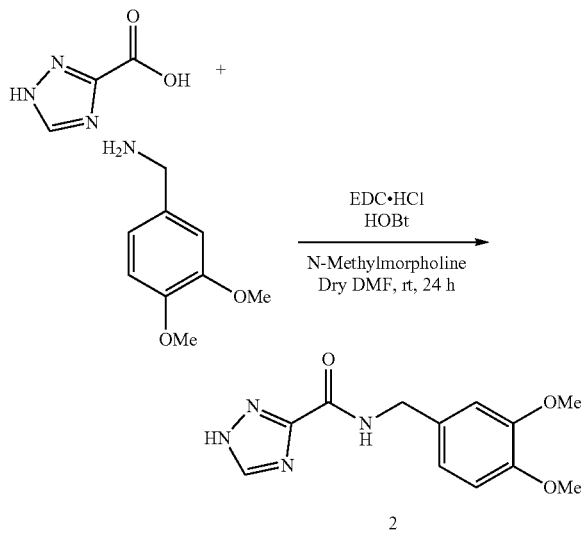

To a reaction of 1H-1,2,4-triazole-3-carboxylic acid (226 mg, 2.0 mmol) and (3,4-dimethoxybenzyl)amine (0.32 mL, 2.1 mmol) in dry DMF (10 mL) was added 1-hydroxybenzotriazole monohydrate (337 mg, 2.2 mmol) and EDC (N-(3-Dimethylaminopropyl)-N'-ethylcarbodiimide) (422 mg, 2.2 mmol) followed by N-methylmorpholine (0.88 mL, 8.0 mmol via syringe). The mixture was stirred at room temperature under nitrogen and the solids were gradually dissolved. The contents were stirred at room temperature for 24 h, and then slowly diluted into iced water and extracted with DCM (50 mL×2). The DCM phase was washed with ice cold water (2×100 mL). The DCM phase was dried over anhydrous $Na_2SO_4$, filtered and concentrated under reduced pressure and chromatographed on silica gel using EtOAc and Hexanes (70:30) as eluents to get the desired amide 2 (40.7 mg, 8% yield) as a white solid. $^1$H-NMR (400 MHz, DMSO-$d_6$): δ14.74-14.50 (m, 1H), 9.06 (br s, 1H), 8.48-8.46 (m, 1H), 6.97 (m, 1H), 6.90-6.88 (m, 1H), 6.85-6.83 (m, 1H), 4.37 (d, J=6.4 Hz, 2H), 3.73 (d, J=3.6 Hz, 6H) ppm. MH+=263.2 m/z.

Synthesis of 3

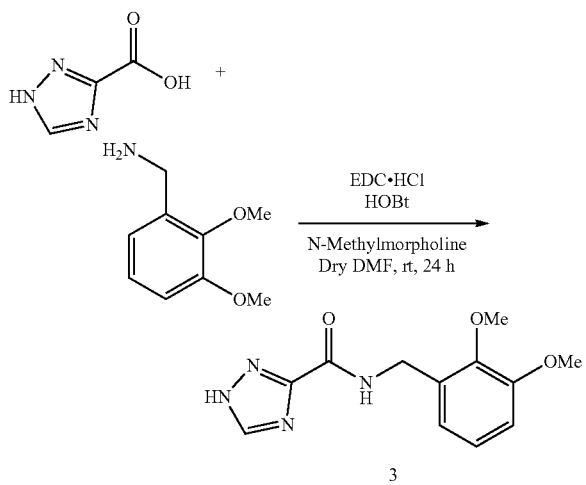

To a reaction of 1H-1,2,4-triazole-3-carboxylic acid (226 mg, 2.0 mmol) and (2,3-dimethoxybenzyl)amine (0.31 mL, 2.1 mmol) in dry DMF (10 mL) was added 1-hydroxybenzotriazole monohydrate (337 mg, 2.2 mmol) and EDC (N-(3-Dimethylaminopropyl)-N'-ethylcarbodiimide) (422 mg, 2.2 mmol) followed by N-methylmorpholine (0.88 mL, 8.0 mmol via syringe). The mixture was stirred at room temperature under nitrogen and the solids were gradually dissolved. The contents were stirred at room temperature for 24 h, and then slowly diluted into ice cold water and extracted with DCM (2×50 mL). The DCM phase was washed with ice cold water (2×100 mL). The DCM phase was dried over anhydrous $Na_2SO_4$, filtered and concentrated under reduced pressure and chromatographed on silica gel using EtOAc and Hexanes (9:1) as eluents to get the desired amide 3 (104.9 mg, 20% yield) as a white solid. $^1$H-NMR (400 MHz, DMSO-$d_6$): δ14.67 (br s, 1H), 8.94 (br s, 1H), 8.49 (br s, 1H), 7.03-6.99 (m, 1H), 6.99-6.94 (m, 1H), 6.85-6.82 (m, 1H), 4.48 (d, J=6.4 Hz, 2H), 3.80 (s, 3H), 3.78 (s, 3H) ppm. MH+=233.2 m/z.

Synthesis of 4

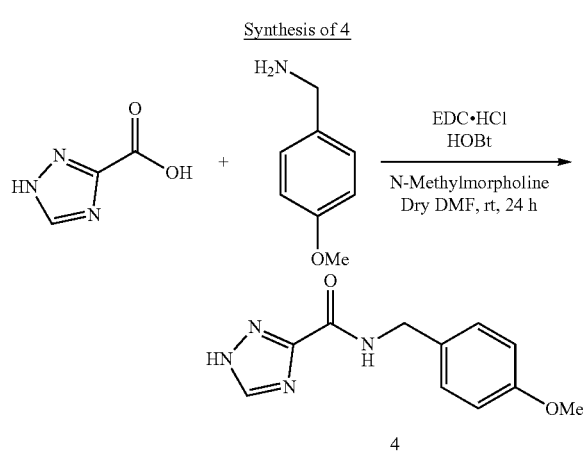

To a reaction of 1H-1,2,4-triazole-3-carboxylic acid (226 mg, 2.0 mmol) and (4-methoxyphenyl)methanamine (0.27 mL, 2.1 mmol) in dry DMF (10 mL) was added 1-hydroxybenzotriazole monohydrate (337 mg, 2.2 mmol) and EDC (N-(3-Dimethylaminopropyl)-N'-ethylcarbodiimide) (422 mg, 2.2 mmol) followed by N-methylmorpholine (0.88 mL, 8.0 mmol via syringe). The mixture was stirred at room temperature under nitrogen and the solids were gradually dissolved. The contents were stirred at room temperature for 24.0 h, and then slowly diluted into iced water and extracted with DCM (2×50 mL). The DCM phase was washed with ice cold water (2×100 mL). The DCM phase was dried over anhydrous Na$_2$SO$_4$, filtered and concentrated under reduced pressure and chromatographed on silica gel using MeOH/EtOAc/DCM (6:50:50, v/v/v) as eluents to get the desired amide 4 (137 mg, 29% yield) as a white solid. $^1$H-NMR (400 MHz, DMSO-d$_6$): δ14.70-14.61 (m, 1H), 9.07 (br s, 1H), 8.45 (br s, 1H), 7.24 (d, J=8.4 Hz, 2H), 6.87 (d, J=8.8 Hz, 2H), 4.36 (d, J=6.4 Hz, 2H), 3.72 (s, 3H) ppm. MH$^+$=233.2 m/z.

Synthesis of 5

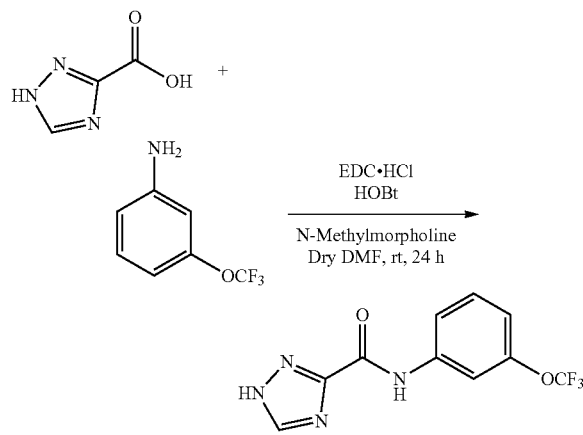

To a reaction of 1H-1,2,4-triazole-3-carboxylic acid (226 mg, 2.0 mmol) and 3-(trifluoromethoxy)aniline (0.28 mL, 2.1 mmol) in dry DMF (10 mL) was added 1-hydroxybenzotriazole monohydrate (337 mg, 2.2 mmol) and EDC (N-(3-Dimethylaminopropyl)-N'-ethylcarbodiimide) (422 mg, 2.2 mmol) followed by N-methylmorpholine (0.88 mL, 8.0 mmol via syringe). The mixture was stirred at room temperature under nitrogen and the solids were gradually dissolved. The contents were stirred at room temperature for 24.0 h, and then slowly diluted into iced water and extracted with DCM (2×50 mL). The DCM phase was washed with ice cold water (2×100 mL). The DCM phase was dried over anhydrous Na$_2$SO$_4$, concentrated under reduced pressure and chromatographed on silica gel using EtOAc and Hexanes (50:50) as eluents to get the desired amide 5 (123.8 mg, 23% yield) as a white solid. $^1$H-NMR (400 MHz, DMSO-d$_6$): δ14.89-14.74 (m, 1H), 10.82 (br s, 1H), 8.67 (br s, 1H), 8.00 (br s, 1H), 7.88 (d, J=8 Hz, 1H), 7.49 (t, J=8.2 Hz, 1H), 7.11 (d, J=8 Hz, 1H); $^{19}$F-NMR (376 MHz, DMSO-d$_6$): δ−56.69 ppm. MH$^+$=273.2 m/z.

Synthesis of 6

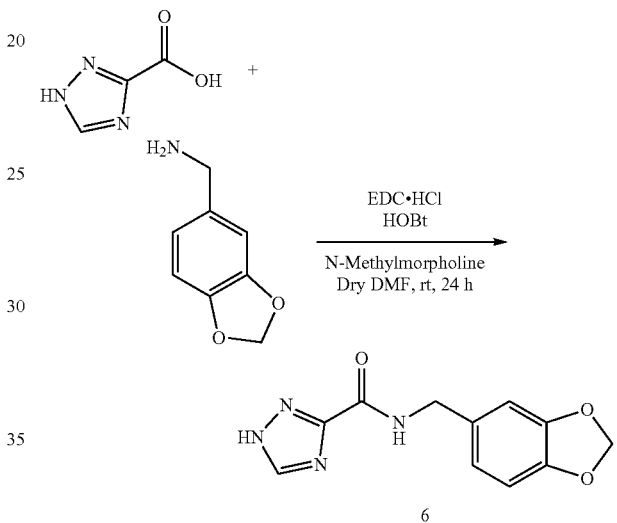

To a reaction of 1H-1,2,4-triazole-3-carboxylic acid (226 mg, 2.0 mmol) and Piperonylamine (0.26 mL, 2.1 mmol) in dry DMF (10 mL) was added 1-hydroxybenzotriazole monohydrate (337 mg, 2.2 mmol) and EDC (N-(3-Dimethylaminopropyl)-N'-ethylcarbodiimide) (422 mg, 2.2 mmol) followed by N-methylmorpholine (0.88 mL, 8.0 mmol via syringe). The mixture was stirred at room temperature under nitrogen and the solids were gradually dissolved. The contents were stirred at room temperature for 24.0 h, and then slowly diluted into iced water and extracted with DCM (2×50 mL). The DCM phase was washed with ice cold water (2×100 mL). The DCM phase was dried over anhydrous Na$_2$SO$_4$, filtered and concentrated under reduced pressure and chromatographed on silica gel using EtOAc as eluents to get the desired amide 6 (95 mg, 19% yield) as a white solid. $^1$H-NMR (400 MHz, DMSO-d$_6$): δ15.58-13.83 (m, 1H), 9.10 (br s, 1H), 8.47 (br s, 1H), 6.90-6.78 (m, 3H), 5.97 (s, 2H), 4.36 (d, J=6.4 Hz, 2H) ppm. MH$^+$=247.1 m/z.

Synthesis of 7

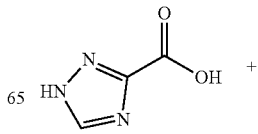

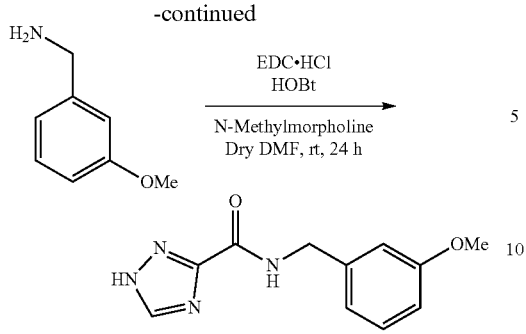

7

To a reaction of 1H-1,2,4-triazole-3-carboxylic acid (226 mg, 2.0 mmol) and 3-methoxybenzylamine (0.28 mL, 2.2 mmol) in dry DMF (10 mL) was added 1-hydroxybenzotriazole monohydrate (337 mg, 2.2 mmol) and EDC (N-(3-Dimethylaminopropyl)-N'-ethylcarbodiimide) (422 mg, 2.2 mmol) followed by N-methylmorpholine (0.88 mL, 8.0 mmol via syringe). The mixture was stirred at room temperature under nitrogen and the solids were gradually dissolved. The contents were stirred at room temperature for 24.0 h, and then slowly diluted into iced water and extracted with DCM (2×50 mL). The DCM phase was washed with ice cold water (2×100 mL). The DCM phase was dried over anhydrous $Na_2SO_4$, concentrated under reduced pressure and chromatographed on silica gel using MeOH and DCM (2:98) as eluents to get the desired amide 7 (170.9 mg, 37% yield) as a white solid compound. $^1$H-NMR (400 MHz, DMSO-$d_6$): δ14.76-14.65 (m, 1H), 9.15 (br s, 1H), 8.48 (br s, 1H), 7.23 (t, J=8 Hz, 1H), 6.90-6.88 (m, 2H), 6.82-6.80 (m, 1H), 4.43 (d, J=6 Hz, 2H), 3.73 (s, 3H) ppm. MH$^+$=233.2 m/z.

Synthesis of 8

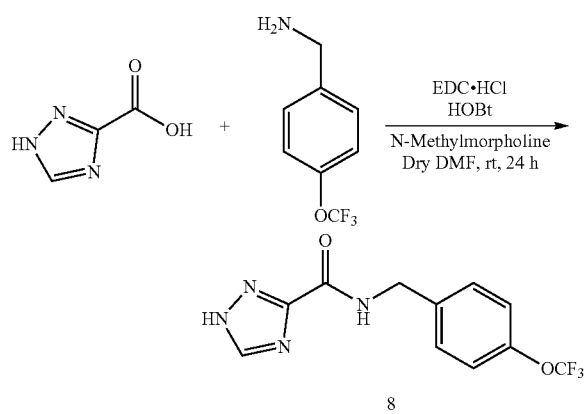

8

To a reaction of 1H-1,2,4-triazole-3-carboxylic acid (113 mg, 1.19 mmol) and 4-(trifluoromethoxy)benzylamine (0.20 mL, 1.31 mmol) in dry DMF (10 mL) was added 1-hydroxybenzotriazole monohydrate (200 mg, 1.31 mmol) and EDC (N-(3-Dimethylaminopropyl)-N'-ethylcarbodiimide) (251 mg, 1.31 mmol) followed by N-methylmorpholine (0.52 mL, 4.76 mmol via syringe). The mixture was stirred at room temperature under nitrogen and the solids were gradually dissolved. The contents were stirred at room temperature for 24 h, and then slowly diluted into iced water and extracted with DCM (2×50 mL). The DCM phase was washed with ice cold water (2×100 mL). The DCM phase was dried over anhydrous $Na_2SO_4$, concentrated under reduced pressure and chromatographed on silica gel using MeOH and DCM (8:92) as eluents to get the desired amide 8 (305.3 mg, 90% yield) as a white solid compound. $^1$H-NMR (400 MHz, DMSO-$d_6$): δ14.80-14.01 (br s, 1H), 9.25 (br s, 1H), 8.50 (br s, 1H), 7.44 (d, J=8.4 Hz, 2H), 7.32 (d, J=8 Hz, 2H), 4.47 (d, J=6 Hz, 2H); $^{19}$F-NMR (376 MHz, DMSO-$d_6$): δ−56.89 ppm. MH$^+$=287.2 m/z.

Synthesis of 9

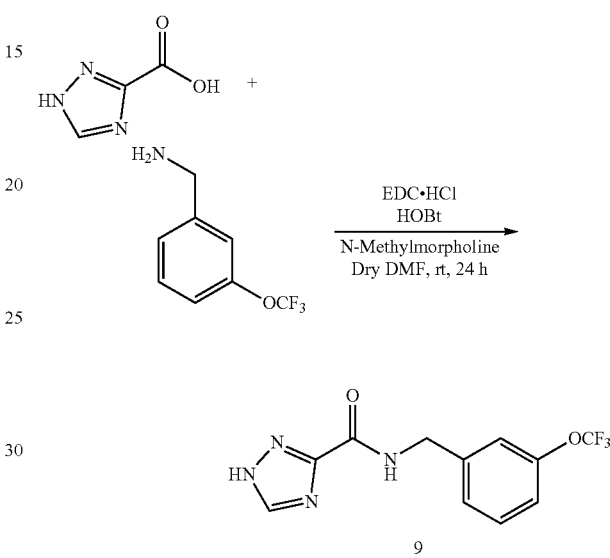

9

To a reaction of 1H-1,2,4-triazole-3-carboxylic acid (113 mg, 1.19 mmol) and 3-(trifluoromethoxy)benzylamine (250 mg, 1.31 mmol) in dry DMF (10 mL) was added 1-hydroxybenzotriazole monohydrate (200 mg, 1.31 mmol) and EDC (N-(3-Dimethylaminopropyl)-N'-ethylcarbodiimide) (251 mg, 1.31 mmol) followed by N-methylmorpholine (0.52 mL, 4.76 mmol via syringe). The mixture was stirred at room temperature under nitrogen and the solids were gradually dissolved. The contents were stirred at room temperature for 24.0 h, and then slowly diluted into iced water and extracted with DCM (2×50 mL). The DCM phase was washed with ice cold water (2×100 mL). The DCM phase was dried over anhydrous $Na_2SO_4$, filtered and concentrated under reduced pressure and chromatographed on silica gel using DCM and EtOAc (10:90) as eluents to get the desired amide 9 (108.7 mg, 32% yield) as a white solid compound. $^1$H-NMR (400 MHz, DMSO-$d_6$): δ14.67 (br s, 1H), 9.28 (br s, 1H), 8.53 (br s, 1H), 7.48-7.44 (m, 1H), 7.36-7.34 (m, 1H), 7.30 (br s, 1H), 7.24-7.22 (m, 1H), 4.50 (d, J=6.4 Hz, 2H); $^{19}$F-NMR (376 MHz, DMSO-$d_6$): δ−56.70 ppm. MH$^+$=287.2 m/z.

Synthesis of 10

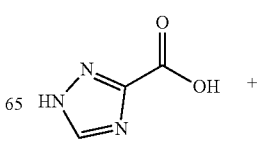

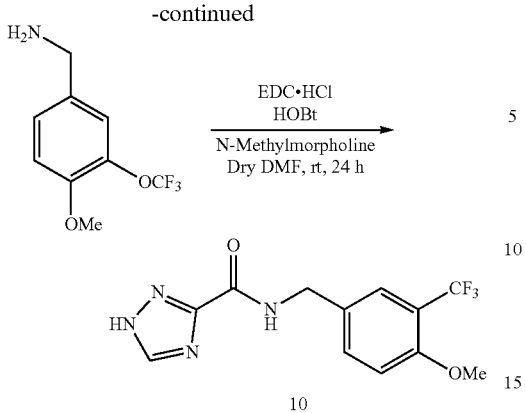

10

To a reaction of 1H-1,2,4-triazole-3-carboxylic acid (100 mg, 0.87 mmol) and 4-Methoxy-3-(trifluoromethyl)benzylamine (200 mg, 0.97 mmol) in dry DMF (10 mL) was added 1-hydroxybenzotriazole monohydrate (146 mg, 0.97 mmol) and EDC (N-(3-Dimethylaminopropyl)-N'-ethylcarbodiimide) (186 mg, 0.97 mmol) followed by N-methylmorpholine (0.38 mL, 3.48 mmol via syringe). The mixture was stirred at room temperature under nitrogen and the solids were gradually dissolved. The contents were stirred at room temperature for 24.0 h, and then slowly diluted into iced water and extracted with DCM (2×50 mL). The DCM phase was washed with ice cold water (2×100 mL). The DCM phase was dried over anhydrous $Na_2SO_4$, filtered and concentrated under reduced pressure and chromatographed on silica gel using EtOAc as eluents to get the desired amide 10 (62.8 mg, 24% yield) as a white solid compound. $^1$H-NMR (400 MHz, DMSO-$d_6$): δ14.66 (br s, 1H), 9.23 (br s, 1H), 8.49 (br s, 1H), 7.60-7.58 (m, 2H), 7.22 (d, J=8.4 Hz, 1H), 4.43 (d, J=6 Hz, 2H), 3.86 (s, 3H); $^{19}$F-NMR (376 MHz, DMSO-$d_6$): δ−60.82 ppm. MH$^+$=301.4 m/z.

Synthesis of 11

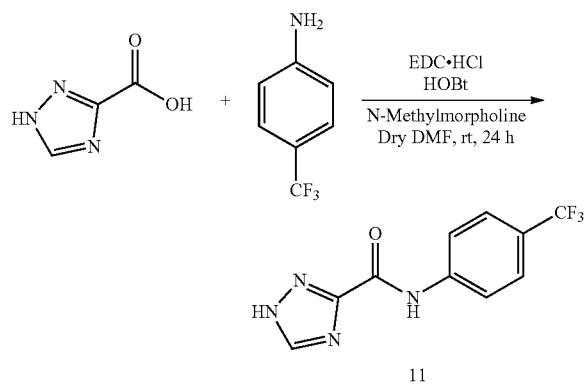

11

To a reaction of 1H-1,2,4-triazole-3-carboxylic acid (226 mg, 2.0 mmol) and 4-(trifluoromethyl)aniline (0.28 mL, 2.2 mmol) in dry DMF (10 mL) was added 1-hydroxybenzotriazole monohydrate (337 mg, 2.2 mmol) and EDC (N-(3-Dimethylaminopropyl)-N'-ethylcarbodiimide) (422 mg, 2.2 mmol) followed by N-methylmorpholine (0.88 mL, 8.0 mmol via syringe). The mixture was stirred at room temperature under nitrogen and the solids were gradually dissolved. The contents were stirred at room temperature for 24.0 h, and then slowly diluted into iced water and extracted with DCM (2×50 mL). The DCM phase was washed with ice cold water (2×100 mL). The DCM phase was dried over anhydrous $Na_2SO_4$, concentrated under reduced pressure and chromatographed on silica gel using EtOAc and Hexanes (80:20) as eluents to get the desired amide 11 (44.4 mg, 9% yield) as a white solid compound. $^1$H-NMR (400 MHz, DMSO-$d_6$): δ14.86 (br s, 1H), 10.90 (br s, 1H), 8.70 (br s, 1H), 8.12 (d, J=8 Hz, 2H), 7.75 (d, J=8 Hz, 2H); $^{19}$F-NMR (376 MHz, DMSO-$d_6$): δ−60.46 ppm. MH$^+$=257.0 m/z.

Synthesis of 12

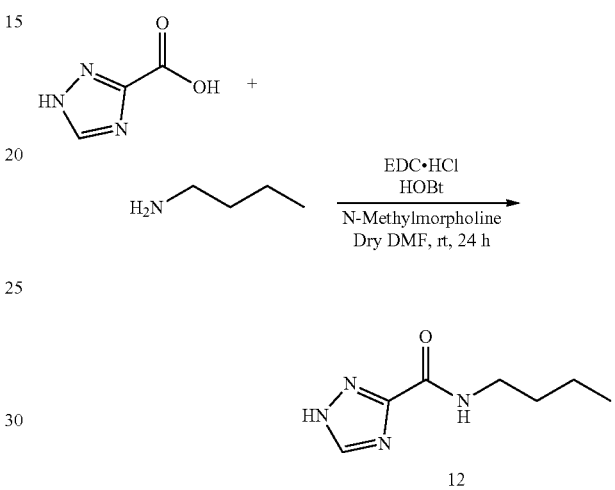

12

To a reaction of 1H-1,2,4-triazole-3-carboxylic acid (226 mg, 2.0 mmol) and butan-1-amine (0.21 mL, 2.1 mmol) in dry DMF (10 mL) was added 1-hydroxybenzotriazole monohydrate (337 mg, 2.2 mmol) and EDC (N-(3-Dimethylaminopropyl)-N'-ethylcarbodiimide) (422 mg, 2.2 mmol) followed by N-methylmorpholine (0.88 mL, 8.0 mmol via syringe). The mixture was stirred at room temperature under nitrogen and the solids were gradually dissolved. The contents were stirred at room temperature for 24.0 h, and then slowly diluted into iced water and extracted with DCM (2×50 mL). The DCM phase was washed with ice cold water (2×100 mL). The DCM phase was dried over anhydrous $Na_2SO_4$, filtered and concentrated under reduced pressure and chromatographed on silica gel using EtOAc and Hexanes (80:20) as eluents to get the desired amide 12 (32 mg, 10% yield) as a white solid compound. $^1$H-NMR (400 MHz, DMSO-$d_6$): δ14.75-14.44 (m, 1H), 8.58 (br s, 1H), 8.41 (br s, 1H), 3.26-3.20 (m, 2H), 1.54-1.45 (m, 2H), 1.35-1.23 (m, 2H), 0.89 (t, J=7.2 Hz, 3H) ppm. MH$^+$=169.2 m/z.

Synthesis of 13

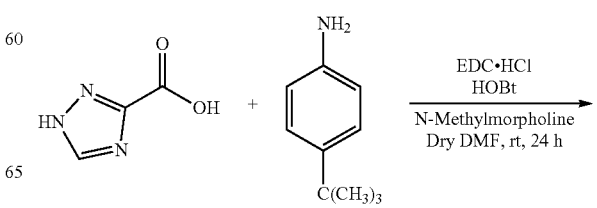

-continued

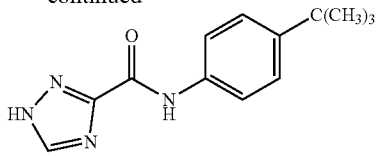

13

To a reaction of 1H-1,2,4-triazole-3-carboxylic acid (226 mg, 2.0 mmol) and 4-(tert-butyl)aniline (0.33 mL, 2.1 mmol) in dry DMF (10 mL) was added 1-hydroxybenzotriazole monohydrate (337 mg, 2.2 mmol) and EDC (N-(3-Dimethylaminopropyl)-N'-ethylcarbodiimide) (422 mg, 2.2 mmol) followed by N-methylmorpholine (0.88 mL, 8.0 mmol via syringe). The mixture was stirred at room temperature under nitrogen and the solids were gradually dissolved. The contents were stirred at room temperature for 24.0 h, and then slowly diluted into iced water and extracted with DCM (2×50 mL). The DCM phase was washed with ice cold water (2×100 mL). The DCM phase was dried over anhydrous $Na_2SO_4$, filtered and concentrated under reduced pressure and chromatographed on silica gel using EtOAc and Hexanes (60:40) as eluents to get the desired amide 13 (123 mg, 25% yield) as a white solid compound. $^1$H-NMR (400 MHz, DMSO-$d_6$): δ14.84-14.72 (m, 1H), 10.42 (br s, 1H), 8.58 (br s, 1H), 7.74 (d, J=8.8 Hz, 2H), 7.37 (d, J=8.4 Hz, 2H), 1.28 (s, 9H) ppm. MH$^+$=245.2 m/z.

Synthesis of 14

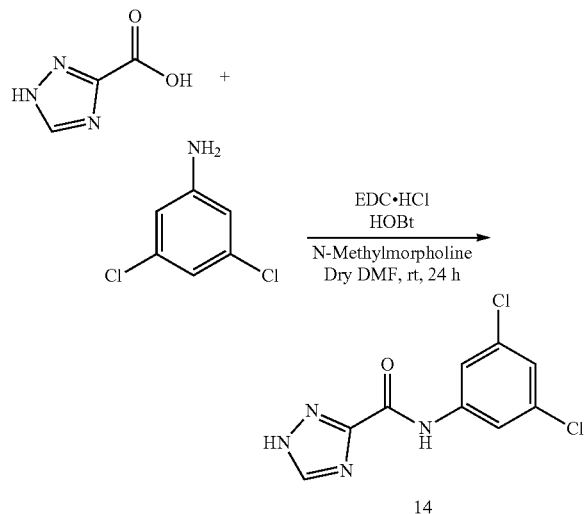

14

To a reaction of 1H-1,2,4-triazole-3-carboxylic acid (226 mg, 2.0 mmol) and 3,5-dichloroaniline (340 mg, 2.1 mmol) in dry DMF (10 mL) was added 1-hydroxybenzotriazole monohydrate (337 mg, 2.2 mmol) and EDC (N-(3-Dimethylaminopropyl)-N'-ethylcarbodiimide) (422 mg, 2.2 mmol) followed by N-methylmorpholine (0.88 mL, 8.0 mmol via syringe). The mixture was stirred at room temperature under nitrogen and the solids were gradually dissolved. The contents were stirred at room temperature for 24.0 h, and then slowly diluted into iced water and extracted with DCM (2×50 mL). The DCM phase was washed with ice cold water (2×100 mL). The DCM phase was dried over anhydrous $Na_2SO_4$, filtered and concentrated under reduced pressure and chromatographed on silica gel using EtOAc and Hexanes (60:40) as eluents to get the desired amide 14 (68.6 mg, 13% yield) as a white solid compound. $^1$H-NMR (400 MHz, DMSO-$d_6$): δ14.85 (br s, 1H), 10.88 (br s, 1H), 8.69 (br s, 1H), 8.04-7.98 (m, 2H), 7.35-7.33 (m, 1H) ppm. MH$^+$=257.3 m/z.

Synthesis of 15

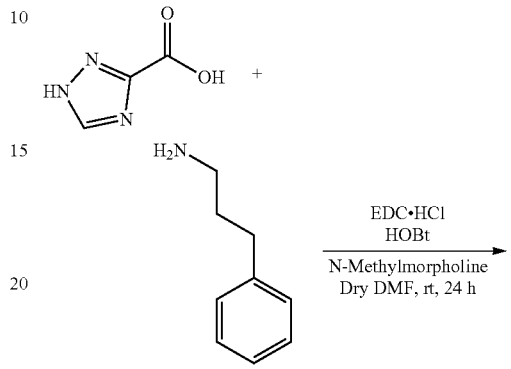

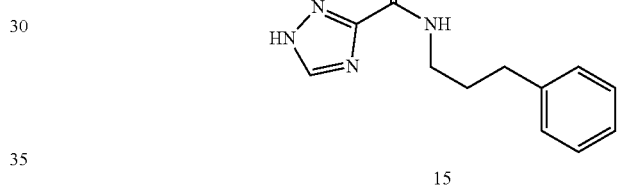

15

To a reaction of 1H-1,2,4-triazole-3-carboxylic acid (226 mg, 2.0 mmol) and 3-phenylpropan-1-amine (0.30 mL, 2.1 mmol) in dry DMF (10 mL) was added 1-hydroxybenzotriazole monohydrate (337 mg, 2.2 mmol) and EDC (N-(3-Dimethylaminopropyl)-N'-ethylcarbodiimide) (422 mg, 2.2 mmol) followed by N-methylmorpholine (0.88 mL, 8.0 mmol via syringe). The mixture was stirred at room temperature under nitrogen and the solids were gradually dissolved. The contents were stirred at room temperature for 24.0 h, and then slowly diluted into iced water and extracted with DCM (2×50 mL). The DCM phase was washed with ice cold water (2×100 mL). The DCM phase was dried over anhydrous $Na_2SO_4$, filtered and concentrated under reduced pressure and chromatographed on silica gel using EtOAc as eluents to get the desired amide 15 (69.7 mg, 15% yield) as a white solid compound. $^1$H-NMR (400 MHz, DMSO-$d_6$): δ14.63 (br s, 1H), 8.68 (br s, 1H), 8.42 (br s, 1H), 7.30-7.18 (m, 5H), 3.40-3.24 (m, 2H), 2.61 (t, J=7.6 Hz, 2H), 1.87-1.78 (m, 2H) ppm. MH$^+$=231.3 m/z.

Synthesis of 16

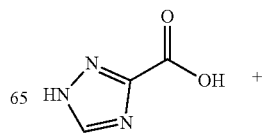

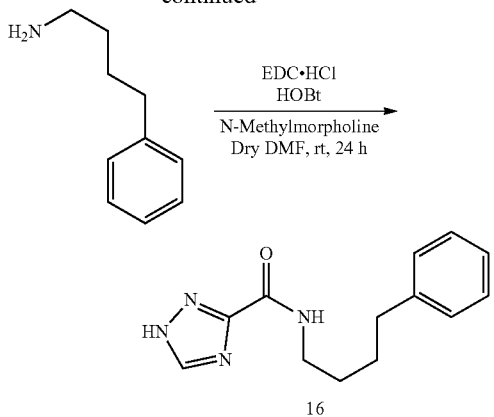

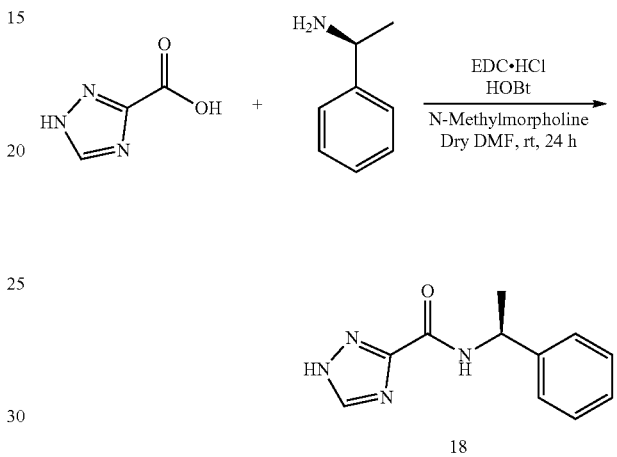

Synthesis of 18

To a reaction of 1H-1,2,4-triazole-3-carboxylic acid (226 mg, 2.0 mmol) and 4-phenylbutan-1-amine (0.33 mL, 2.1 mmol) in dry DMF (10 mL) was added 1-hydroxybenzotriazole monohydrate (337 mg, 2.2 mmol) and EDC (N-(3-Dimethylaminopropyl)-N'-ethylcarbodiimide) (422 mg, 2.2 mmol) followed by N-methylmorpholine (0.88 mL, 8.0 mmol via syringe). The mixture was stirred at room temperature under nitrogen and the solids were gradually dissolved. The contents were stirred at room temperature for 24.0 h, and then slowly diluted into iced water and extracted with DCM (2×50 mL). The DCM phase was washed with ice cold water (2×100 mL). The DCM phase was dried over anhydrous $Na_2SO_4$, filtered and concentrated under reduced pressure and chromatographed on silica gel using EtOAc and Hexanes (75:25) as eluents to get the desired amide 16 (129.1 mg, 25% yield) as a white solid compound. $^1$H-NMR (400 MHz, DMSO-$d_6$): δ14.64 (br s, 1H), 8.64 (br s, 1H), 8.42 (br s, 1H), 7.28-7.24 (m, 2H), 7.20-7.14 (m, 3H), 3.31-3.24 (m, 2H), 2.63-2.56 (m, 2H), 1.68-1.54 (m, 4H) ppm. MH$^+$=245.3 m/z.

Synthesis of 17

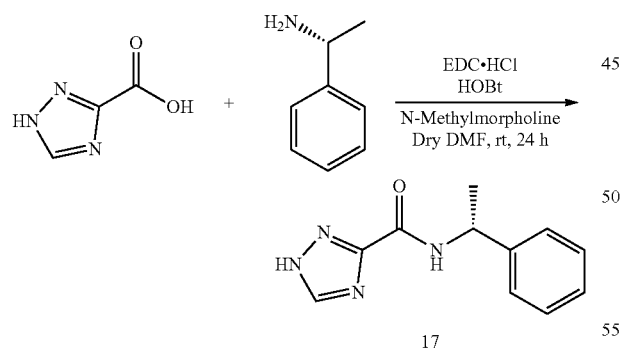

To a reaction of 1H-1,2,4-triazole-3-carboxylic acid (226 mg, 2.0 mmol) and (R)-(+)-α-methyl benzyl amine (0.27 mL, 2.1 mmol) in dry DMF (10 mL) was added 1-hydroxybenzotriazole monohydrate (337 mg, 2.2 mmol) and EDC (N-(3-Dimethylaminopropyl)-N'-ethylcarbodiimide) (422 mg, 2.2 mmol) followed by N-methylmorpholine (0.88 mL, 8.0 mmol via syringe). The mixture was stirred at room temperature under nitrogen and the solids were gradually dissolved. The contents were stirred at room temperature for 24.0 h, and then slowly diluted into iced water and extracted with DCM (2×50 mL). The DCM phase was washed with ice cold water (2×100 mL). The DCM phase was dried over anhydrous $Na_2SO_4$, filtered and concentrated under reduced pressure and chromatographed on silica gel using EtOAc and Hexanes (75:25) as eluents to get the desired amide 17 (88 mg, 20% yield) as a white solid compound. $^1$H-NMR (400 MHz, DMSO-$d_6$): δ14.64 (br s, 1H), 8.97 (br s, 1H), 8.47 (br s, 1H), 7.42-7.40 (m, 2H), 7.34-7.30 (m, 2H), 7.25-7.21 (m, 1H), 5.19-5.12 (m, 1H), 1.50 (d, J=6.8 Hz, 3H) ppm. MH$^+$=217.1 m/z.

Synthesis of 18

To a reaction of 1H-1,2,4-triazole-3-carboxylic acid (226 mg, 2.0 mmol) and (S)-α-methyl benzyl amine (0.27 mL, 2.1 mmol) in dry DMF (10 mL) was added 1-hydroxybenzotriazole monohydrate (337 mg, 2.2 mmol) and EDC (N-(3-Dimethylaminopropyl)-N'-ethylcarbodiimide) (422 mg, 2.2 mmol) followed by N-methylmorpholine (0.88 mL, 8.0 mmol via syringe). The mixture was stirred at room temperature under nitrogen and the solids were gradually dissolved. The contents were stirred at room temperature for 24.0 h, and then slowly diluted into iced water and extracted with DCM (2×50 mL). The DCM phase was washed with ice cold water (2×100 mL). The DCM phase was dried over anhydrous $Na_2SO_4$, filtered and concentrated under reduced pressure and chromatographed on silica gel using EtOAc and Hexanes (75:25) as eluents to get the desired amide 18 (211 mg, 49% yield) as a white solid compound. $^1$H-NMR (400 MHz, DMSO-$d_6$): δ14.67 (br s, 1H), 8.97 (br s, 1H), 8.47 (br s, 1H), 7.42-7.40 (m, 2H), 7.32 (t, J=7.4 Hz, 2H), 7.25-7.21 (m, 1H), 5.20-5.12 (m, 1H), 1.50 (d, J=6.8 Hz, 3H) ppm. MH$^+$=217.1 m/z.

Synthesis of 19

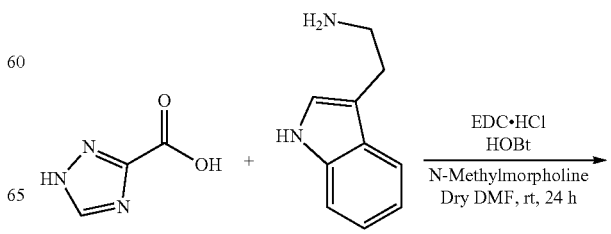

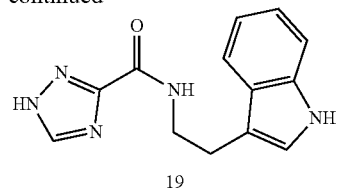

19

To a reaction of 1H-1,2,4-triazole-3-carboxylic acid (226 mg, 2.0 mmol) and 2-(1H-indol-3-yl)ethanamine (0.34 mg, 2.1 mmol) in dry DMF (10 mL) was added 1-hydroxybenzotriazole monohydrate (337 mg, 2.2 mmol) and EDC (N-(3-Dimethylaminopropyl)-N'-ethylcarbodiimide) (422 mg, 2.2 mmol) followed by N-methylmorpholine (0.88 mL, 8.0 mmol via syringe). The mixture was stirred at room temperature under nitrogen and the solids were gradually dissolved. The contents were stirred at room temperature for 24.0 h, and then slowly diluted into iced water and extracted with DCM (2×50 mL). The DCM phase was washed with ice cold water (2×100 mL). The DCM phase was dried over anhydrous $Na_2SO_4$, filtered and concentrated under reduced pressure and chromatographed on silica gel using MeOH and DCM (10:90) as eluents to get the desired amide 19 (193.3 mg, 38% yield) as a white solid compound. $^1$H-NMR (400 MHz, DMSO-$d_6$): δ14.90-14.48 (m, 1H), 10.82 (s, 1H), 8.80-8.13 (m, 2H), 7.61 (d, J=7.6 Hz, 1H), 7.35 (d, J=8 Hz, 1H), 7.21-7.18 (m, 1H), 7.11-7.05 (m, 1H), 7.04-6.96 (m, 1H), 3.61-3.53 (m, 2H), 2.97 (t, J=7.6 Hz, 2H) ppm. $MH^+$=256.2 m/z.

Synthesis of 20

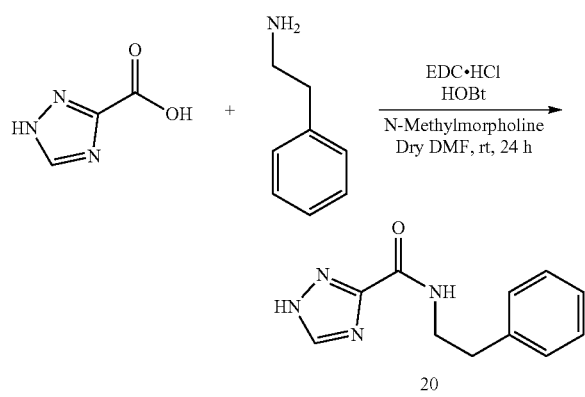

20

To a reaction of 1H-1,2,4-triazole-3-carboxylic acid (226 mg, 2.0 mmol) and 2-phenylethanamine (0.27 mL, 2.1 mmol) in dry DMF (10 mL) was added 1-hydroxybenzotriazole monohydrate (337 mg, 2.2 mmol) and EDC (N-(3-Dimethylaminopropyl)-N'-ethylcarbodiimide) (422 mg, 2.2 mmol) followed by N-methylmorpholine (0.88 mL, 8.0 mmol via syringe). The mixture was stirred at room temperature under nitrogen and the solids were gradually dissolved. The contents were stirred at room temperature for 24.0 h, and then slowly diluted into iced water and extracted with DCM (2×50 mL). The DCM phase was washed with ice cold water (2×100 mL). The DCM phase was dried over anhydrous $Na_2SO_4$, filtered and concentrated under reduced pressure and chromatographed on silica gel using MeOH and DCM (5:95) as eluents to get the desired amide 20 (189.4 mg, 44% yield) as a white solid compound. $^1$H-NMR (400 MHz, DMSO-$d_6$): δ14.63-14.52 (m, 1H), 8.65-8.25 (m, 2H), 7.33-7.17 (m, 5H), 3.55-3.44 (m, 2H), 2.85 (t, J=7.6 Hz, 2H) ppm. $MH^+$=217.1 m/z.

Synthesis of 21

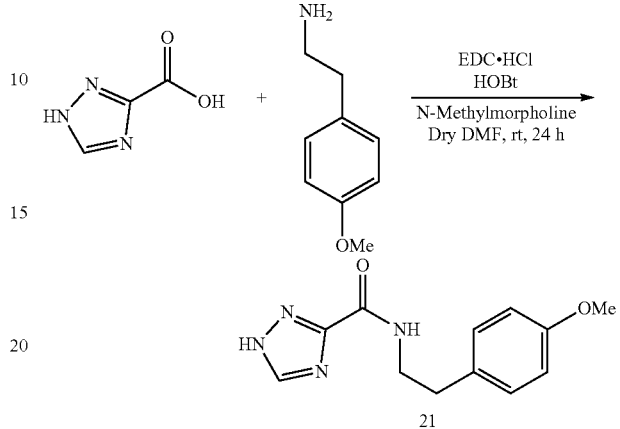

21

To a reaction of 1H-1,2,4-triazole-3-carboxylic acid (226 mg, 2.0 mmol) and 2-(4-methoxyphenyl)ethanamine (0.31 mL, 2.1 mmol) in dry DMF (10 mL) was added 1-hydroxybenzotriazole monohydrate (337 mg, 2.2 mmol) and EDC (N-(3-Dimethylaminopropyl)-N'-ethylcarbodiimide) (422 mg, 2.2 mmol) followed by N-methylmorpholine (0.88 mL, 8.0 mmol via syringe). The mixture was stirred at room temperature under nitrogen and the solids were gradually dissolved. The contents were stirred at room temperature for 24.0 h, and then slowly diluted into iced water and extracted with DCM (2×50 mL). The DCM phase was washed with ice cold water (2×100 mL). The DCM phase was dried over anhydrous $Na_2SO_4$, filtered and concentrated under reduced pressure and chromatographed on silica gel using MeOH and DCM (6:94) as eluents to get the desired amide 21 (193 mg, 39% yield) as a white solid compound. $^1$H-NMR (400 MHz, DMSO-$d_6$): δ14.76-14.35 (br s, 1H), 8.80-8.30 (m, 2H), 7.15 (d, J=8.8 Hz, 2H), 6.85 (d, J=8.8 Hz, 2H), 3.72 (s, 3H), 3.48-3.40 (m, 2H), 2.78 (t, J=7.6 Hz, 2H) ppm. $MH^+$=247.1 m/z.

Synthesis of 22

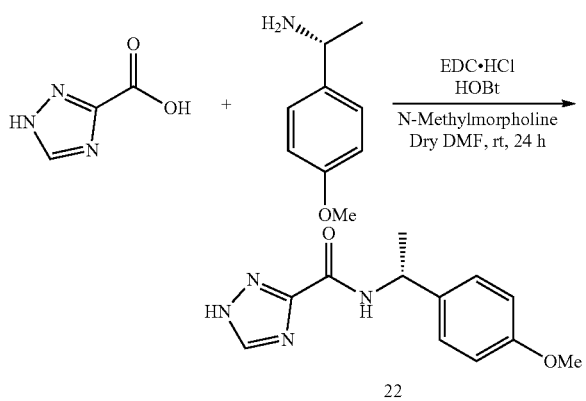

22

To a reaction of 1H-1,2,4-triazole-3-carboxylic acid (226 mg, 2.0 mmol) and (R)-1-(4-methoxyphenyl)ethan-1-amine (0.28 mL, 2.1 mmol) in dry DMF (10 mL) was added 1-hydroxybenzotriazole monohydrate (337 mg, 2.2 mmol) and EDC (N-(3-Dimethylaminopropyl)-N'-ethylcarbodiimide) (422 mg, 2.2 mmol) followed by N-methylmorpholine (0.88 mL, 8.0 mmol via syringe). The mixture was stirred at room temperature under nitrogen and the solids were gradually dissolved. The contents were stirred at room temperature for 24 h, and then slowly diluted into iced water and extracted with DCM (50 mL×2). The DCM phase was washed with ice cold water (100 mL×2). The DCM phase was dried over anhydrous $Na_2SO_4$, filtered and concentrated under reduced pressure and chromatographed on silica gel using MeOH and DCM (5:95) as eluents to get the desired amide 22 (287.1 mg, 58% yield) as a white solid compound. $^1$H-NMR (400 MHz, DMSO-$d_6$): δ14.98-14.44 (m, 1H), 9.16-8.08 (m, 2H), 7.34 (d, J=8.4 Hz, 2H), 6.88 (d, J=8.8 Hz, 2H), 5.18-5.04 (m, 1H), 3.73 (s, 3H), 1.48 (d, J=7.2 Hz, 3H) ppm. $MH^+$=247.1 m/z.

TABLE 2

Compound Solubility

| Compound ID | 16 mg/ml | 10 mM | 1 mM | 100 μM | 10 μM | 1 μM |
|---|---|---|---|---|---|---|
| 1 | DMSO | water | water | water | water | water |
| 2 | DMSO | water | water | water | water | water |
| 3 | DMSO | water | water | water | water | water |
| 4 | DMSO | water | water | water | water | water |
| 5 | DMSO | DMSO | water | water | water | water |
| 6 | DMSO | water | water | water | water | water |
| 7 | DMSO | water | water | water | water | water |
| 8 | DMSO | DMSO | water | water | water | water |
| 9 | DMSO | DMSO | water | water | water | water |
| 10 | DMSO | water | water | water | water | water |
| 11 | DMSO | DMSO | DMSO | water | water | water |
| 12 | DMSO | water | water | water | water | water |
| 13 | DMSO | DMSO | water | water | water | water |
| 14 | DMSO | DMSO | DMSO | water | water | water |
| 15 | DMSO | water | water | water | water | water |
| 16 | DMSO | DMSO | water | water | water | water |
| 17 | DMSO | water | water | water | water | water |
| 18 | DMSO | water | water | water | water | water |
| 19 | DMSO | water | water | water | water | water |
| 20 | DMSO | water | water | water | water | water |
| 21 | DMSO | water | water | water | water | water |
| 22 | DMSO | water | water | water | water | water |

Example 2: Identification of Compounds that Target DksA

The DksA protein is highly conserved among Gram-negative bacteria, making it a potential therapeutic target for a broad range of bacteria. Potential drugable sites in DksA zinc finger domain were assessed. Neither the highly conserved $Cys^{114}$, which is buried deep in DksA globular domain, nor any of the other three cysteine residues in the zinc finger offered potential ligand-binding pockets. The $Asp^{714}$ residue is not only critical for DksA protein function but is also highly conserved among DksA orthologues. An area of negatively charged residues, including $Asp^{64}$, $Asp^{71}$, $Asp^{74}$, $Glu^{79}$, $Glu^{80}$, $Glu^{81}$, and $Glu^{85}$ (FIG. 1A), forms a conserved pocket at the tip of the coiled-coil domain of DksA. The region in the DksA crystal structure (PDB 1TJL) containing the pocket at the tip of DksA coiled-coil domain was selected as a small molecule binding target. The commercially-available ZINC database were used for virtual screening of compounds.

Figure 1C:
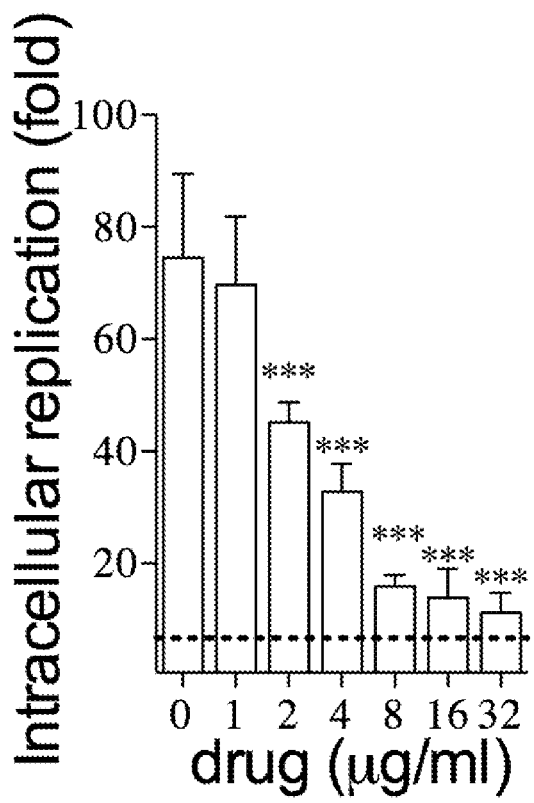
Figure 1D:
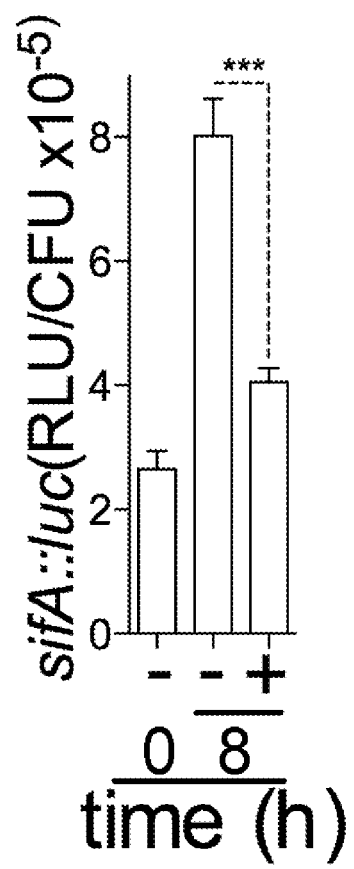
Figure 3:
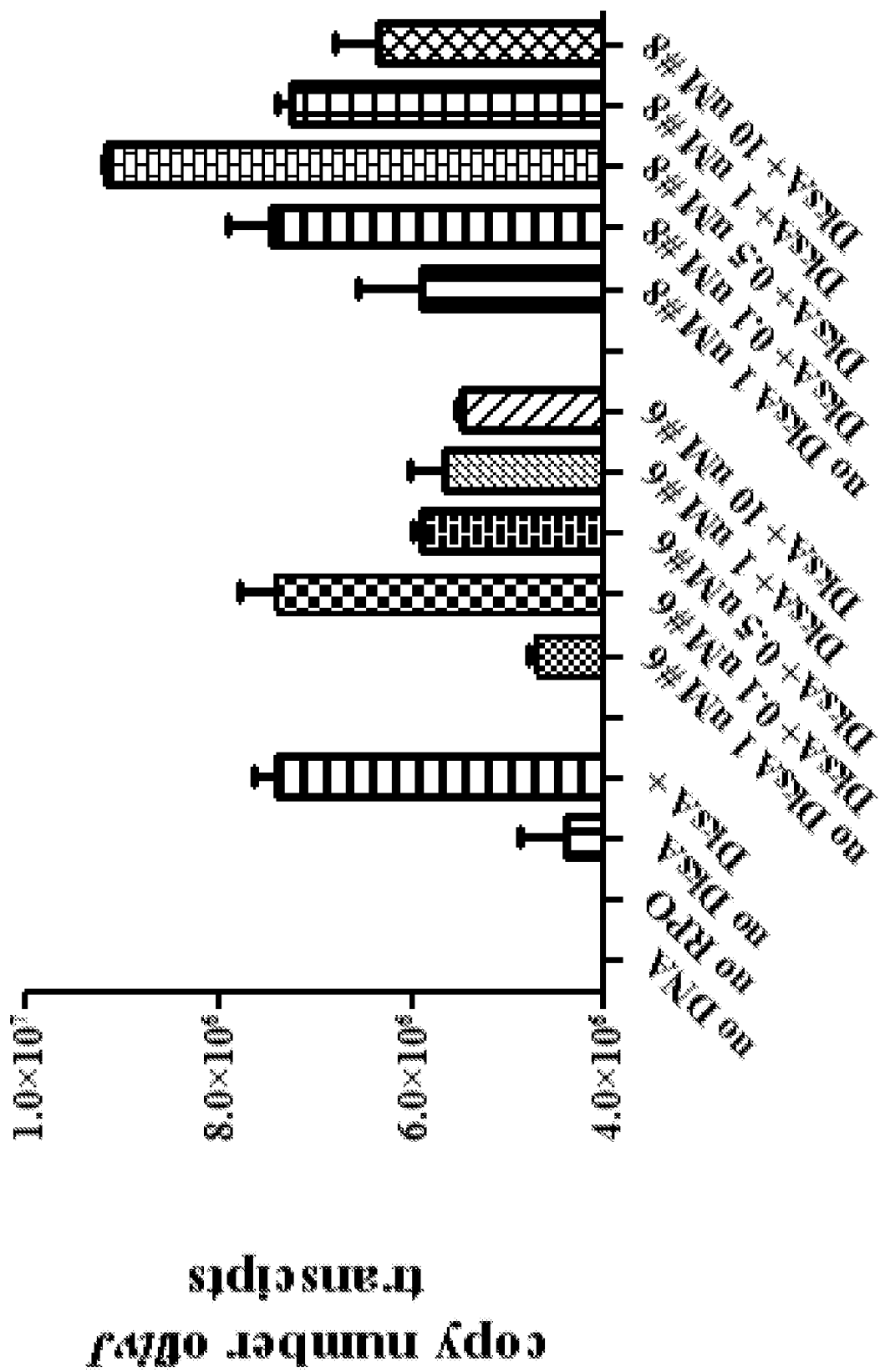
FIG. 3 is a graph showing the effects of increasing concentrations of compounds 1 and 2 on livJ in vitro transcription.
Figure 4:
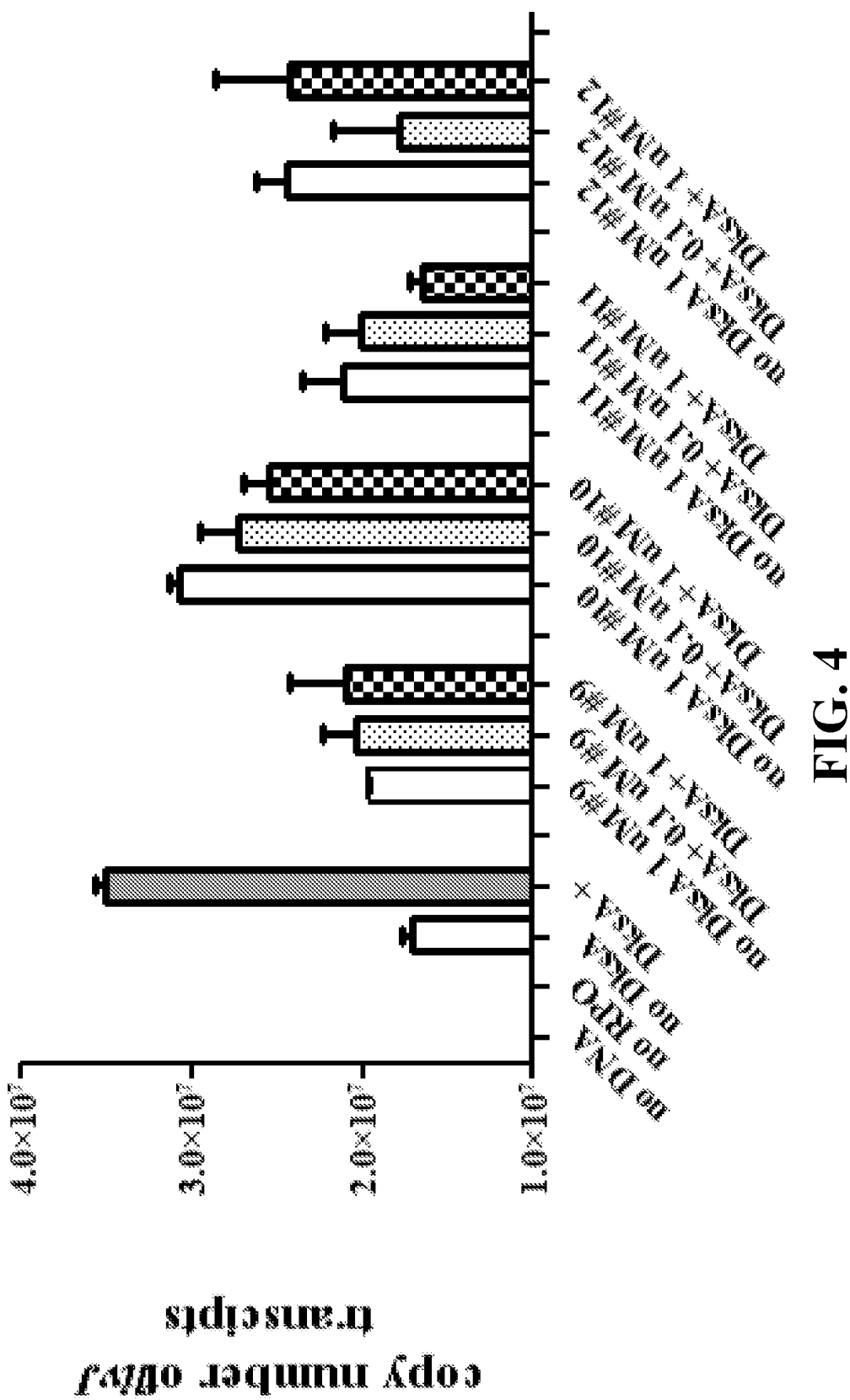
FIG. 4 is a graph showing the effects of increasing concentrations of compounds 3, 4, 5 and 6 on livJ in vitro transcription.
Figure 5:
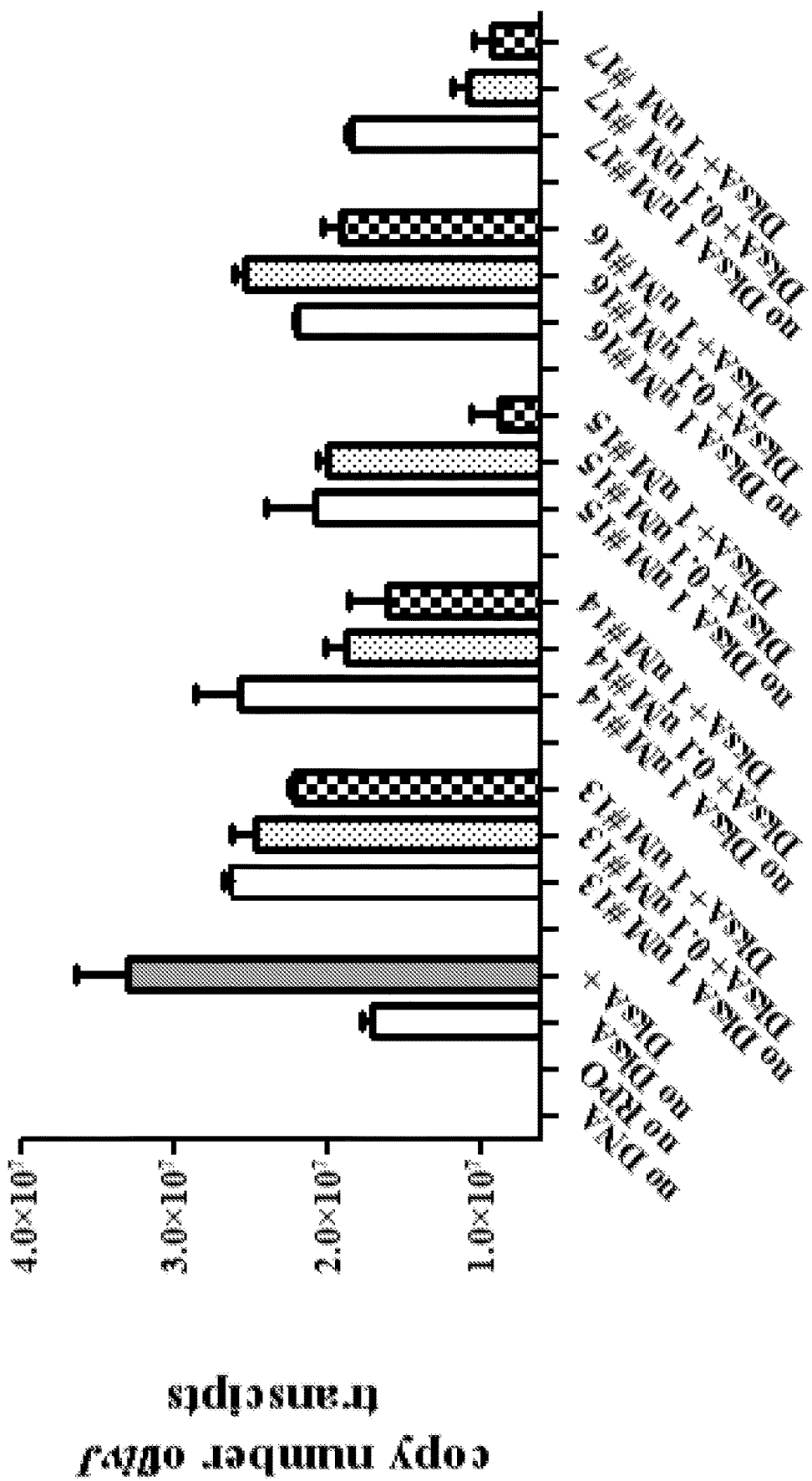
FIG. 5 is a graph showing the effects of increasing concentrations of compounds 7, 8, 9, 10 and 11 on livJ in vitro transcription.
Figure 6:
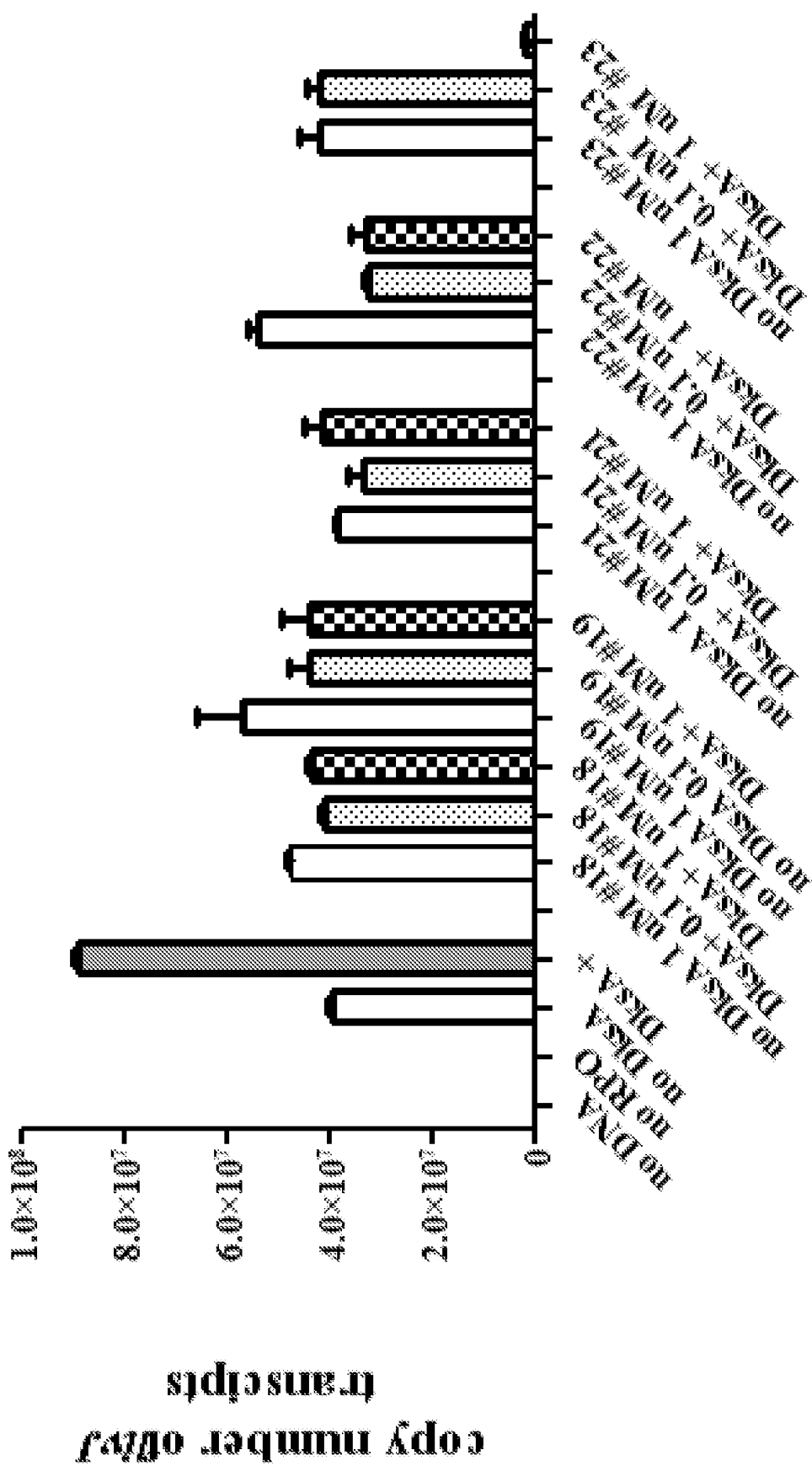
FIG. 6 is a graph showing the effects of increasing concentrations of compounds 12, 13, 14, 15 and 16 on livJ in vitro transcription.
Figure 7:
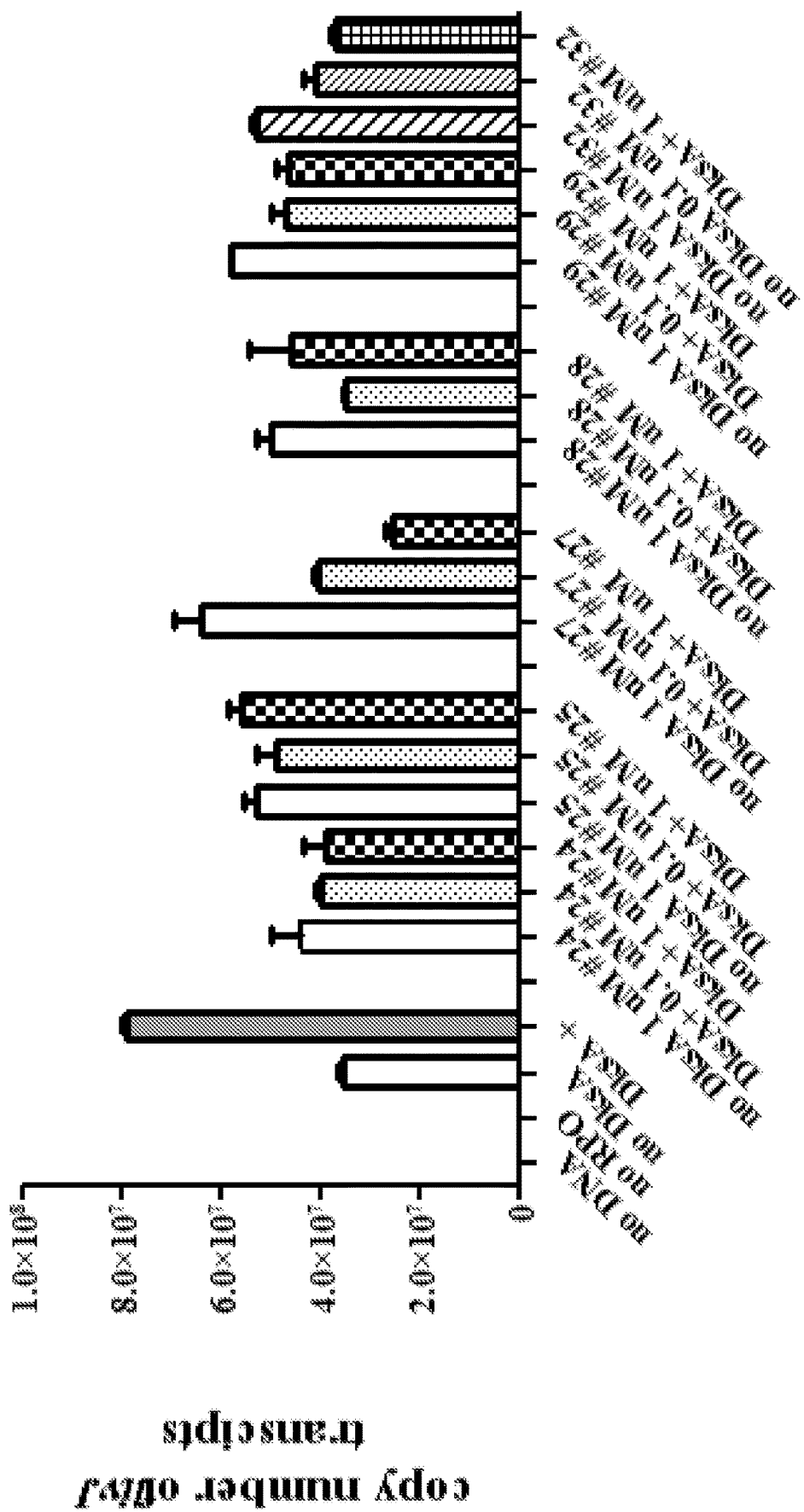
FIG. 7 is a graph showing the effects of increasing concentrations of compounds 17, 18, 19, 20, 21 and 22 on livJ in vitro transcription.

The compounds obtained in this screen were further analyzed for binding to the acidic pocket at the tip of DksA coiled-coil domain using the computer search program Dock. The analysis identified over 400 compounds. A panel of 40 compounds was selected from the top hits based on free energy binding scores. These compounds were investigated using the computer modeling program O. Two additional criteria were applied in order to narrow down the list of candidates: First, the compounds needed to fit deep into the pocket without any clashes; and second, the compounds bound to DksA should have minimal exposed moieties. The compounds selected were further refined according to energy minimization as calculated by the CNS program. 23 compounds were obtained from MolPort and they were tested for their ability to interfere with DksA in a high throughput screen that combined in vitro transcription with highly specific and quantitative qRT-PCR. Five of these compounds, including N-(3,4-dimethoxyphenyl)-1H-1,2,4-triazole-3-carboxamide (1), prevented DksA-mediated repression of rpsM in vitro transcription to some degree. The addition of 1 μM 1 completely inhibited DksA-mediated repression of rpsM in vitro transcription (FIG. 1D). 1 inhibited DksA-mediated repression of rpsM in vitro transcription with an $IC_{50}$ value of 725 μM, which is below the 1 μM target for a screen of this type. As little as 0.1 μM 1 completely inhibited DksA-dependent activation of hisG in vitro transcription. Without intending to be limited to any particular theory, the effect that 1 has on DksA-dependent rpsM or hisG gene transcription is potentially due to differences in promoter activity. Addition of up to 10 μM 1 did not affect rpsM in vitro transcription by the RNA polymerase itself.

Of all of the drugs that inhibited DksA function in the in vitro screens, 1 showed the greatest anti-*Salmonella* activity in disk diffusion assays. DksA controls transcription of metabolic and virulence genes, allowing bacteria to both grow in minimum media and cause disease. Inhibition of bacterial growth in EG minimum media was used as an easy and reliable proxy of the DksA-dependent regulation of metabolism. The minimum inhibitory concentration of 1 against both *Salmonella Typhimurium* strain 14028s and *E. coli* strain 3110 was estimated to be 32 μg/ml (i.e., 129 μM). 1 had potent antimicrobial activity against intracellular *Salmonella* growing in macrophages in complex cell culture media containing 10% fetal bovine serum (FIG. 1C), demonstrating excellent penetrability of 1 through cell host membranes. The poor intracellular growth of ΔdksA *Salmonella* was unaffected by 1, suggesting this drug has minimal off-target effects. Compared to EG media, lower concentrations of 1 resulted in the inhibition of *Salmonella* growth in macrophages, likely reflecting inhibition of DksA-dependent regulation of virulence programs. Accordingly, the addition of 1 to *Salmonella*-infected macrophages repressed transcription of a gene encoding a key effector of the SPI2 type III secretion system, whose expression is tightly regulated by DksA. The addition of 32 μg/ml of 1 did not change (p=0.3) the low levels of lactate dehydrogenase (LDH) released from J774 cells 18 h after infection with wild-type or ΔdksA *Salmonella*, indicating this drug was well tolerated by host cells.

In silico modeling was used to inform SAR studies of 1 and DksA (FIG. 2B). Many of the target compounds arrived at through in silico modeling which were found to dock in the pocket at the tip of the DksA coil-coiled region contained a purine-like ring, similar to ATP (FIG. 2C). Further analyses have shown excellent free energy binding scores for UTP, GTP and ATP. Oxygen atoms on the $C_2$ and $C_4$ positions in the pyrimidine ring of UTP make contact with $Glu^{81}$ carboxylic group and $Ala^{77}$ backbone of DksA. Similarly, the amino group at the $C_6$ position of ATP binds to $Glu^{80}$ carboxylic oxygen and $Ala^{77}$ backbone (FIG. 2C). In addition to interacting with the negatively charge residues at the rim of the pocket, phosphate groups of UTP and ATP establish hydrogen-bonds with $Asn^{68}$ and $Asp^{71}$ that are located deep in the pocket. DksA $Glu^{80}$ and $Glu^{81}$ at the rim of the pocket are also likely to help in the docking of 1 via hydrogen-bonding with N atoms in the carboxamide and the triazole group (FIG. 2D). In contrast to UTP and ATP, however, 1 does not interact with residues deep in the pocket.

Example 3: Inhibition Assays Using Analogues of 1

In a non-limiting example, wild-type *Salmonella* strain 14028s was grown overnight (18.5 h), and then diluted in EG minimal media to a density of about $10^5$ CFU/mL. The specimens were transferred to 3 ml to 14 ml tubes, and treated with the compound of interest to a final concentration of 32, 16, 8, 4, 2, or 1 mg/mL. Each test tube was incubated at 37° C. with shaking for 18 h and bacterial growth was evaluated. The MIC value was determined as the lowest concentration of compound that inhibited growth.

TABLE 3

Minimum inhibitory concentration

| Cmpd. ID | Concentration tested | | | | | | MIC (µg/ml) |
|---|---|---|---|---|---|---|---|
| | 32 µg/ml | 16 µg/ml | 8 µg/ml | 4 µg/ml | 2 µg/ml | 1 µg/ml | |
| 1 | -- | + | + | + | + | + | 32 |
| 2 | + | + | + | + | + | + | ND |
| 3 | -- | +/- | + | + | + | + | 32 |
| 4 | -- | -- | -- | + | + | + | 8 |
| 5 | + | + | + | + | + | + | ND |
| 6 | -- | -- | -- | +/- | + | + | 8 |
| 7 | -- | -- | -- | + | + | + | 8 |
| 8 | + | + | + | + | + | + | ND |
| 9 | + | + | + | + | + | + | ND |
| 10 | + | + | + | + | + | + | ND |
| 11 | + | + | + | + | + | + | ND |
| 12 | -- | -- | -- | + | + | + | 8 |
| 13 | + | + | + | + | + | + | ND |
| 14 | -- | -- | -- | + | + | + | 8 |
| 15 | -- | -- | + | + | + | + | 16 |
| 16 | -- | -- | +/- | + | + | + | 16 |
| 17 | + | + | + | + | + | + | ND |
| 18 | + | + | + | + | + | + | ND |
| 19 | -- | -- | + | + | + | + | 16 |
| 20 | -- | -- | -- | + | + | + | 8 |
| 21 | - | + | + | + | + | + | 32 |
| 22 | + | + | + | + | + | + | ND |

-- (No growth in EG)
+ (Growth in EG)

Example 4: In Vitro Transcription Assays Using Analogues of 1

Compounds that showed MIC values of <16 µg/ml were evaluated for inhibition of DksA-dependent in vitro transcription reactions as described elsewhere herein (Materials and Methods section). The compounds were initially tested at 0.1 µM and 1 µM using as a target the promoter of the livJ gene that encodes a transporter of branch-chain amino acids (Table 4). Compounds that showed activity at 0.1 µM were selected for further study and $IC_{50}$ values were determined using the rpsM gene that encodes a ribosomal protein as the target. The compounds 12, 14, 15, 16, 19 and 20 inhibited rpsM in vitro transcription with $IC_{50}$ values of 73, 71, 51, 91, 75, and 90 nM, respectively.

TABLE 4

In vitro transcription assay results

| Compound ID | 0.1 µM | 1 µM | IVT |
|---|---|---|---|
| 1 | no change | good repression | 1 µM |
| 2 | no change | no change | ND |
| 3 | no induction | no induction | 0.1 µM |
| 4 | no change | no change | ND |
| 5 | no induction | no induction | 0.1 µM |
| 6 | no change | no change | ND |
| 7 | no change | no change | ND |
| 8 | no induction | no induction | 0.1 µM |
| 9 | no induction | Repression | 0.1 µM |
| 10 | no change | no induction | 1 µM |
| 11 | good repression | good repression | 0.1 µM |
| 12 | no induction | no induction | 0.1 µM |
| 13 | no induction | no induction | 0.1 µM |
| 14 | no induction | no induction | 0.1 µM |
| 15 | no induction | no induction | 0.1 µM |
| 16 | no induction | good repression | 0.1 µM |
| 17 | no induction | no induction | 0.1 µM |
| 18 | no induction | no induction | 0.1 µM |
| 19 | no induction | no induction | 0.1 µM |
| 20 | no induction | no induction | 0.1 µM |
| 21 | no induction | no induction | 0.1 µM |
| 22 | no induction | no induction | 0.1 µM |

Example 5: Macrophage Killing Assays

*Salmonella* was cleared after genetic or pharmacological inhibition of DksA. The stringent response is regulated by guanosine tetraphosphate and DksA. Bacterial strains unable to produce the stringent response regulator guanosine tetraphosphate cannot establish persistent infections. IFNγ-treated macrophages kill over 99% of wild-type *Salmonella*; however, the remaining 1% survive in a persistent state driven by the stringent response regulator guanosine tetraphosphate. This difference was used to develop a persistent model of in vitro infection.

C57BL/6 mice were used in the assay following the IACUC guidelines. Mice (6-8 weeks) were inoculated intraperitoneally with 1 mg/mL of sodium periodate in PBS. The solution was sterilized by filtering through 0.22 µM filter prior to injection. Peritoneal macrophages were subsequently harvested from mice 4 days post inoculation (dpi). The exudate cells were resuspended in RPMI 1640 medium (Sigma-Aldrich, St. Loius, MO) supplemented with 10% of heat-inactivated FBS, 15 mM HEPES, 2 mM L-glutamine, 1 mM of sodium pyruvate and 100 U/mL of Penicillin and Streptomycin (ThermoFisher Scientific). The peritoneal exudate cells were counted and adjusted to $3.5 \times 10^6$ cells/ml. 100 µl were transferred onto a 96-well plate and incubated in 5% $CO_2$ at 37° C. for 2 days. The cells in the treatment group were treated with interferon-γ (Peprotech Inc.) 24 h before infection with *Salmonella*.

*Salmonella* strains WT14028s and ΔdksA were grown in LB broth at 37° C. with shaking for 20 h. Mouse peritoneal macrophages (with or without treatment of interferon-6) were then challenged with *Salmonella* at an MOI of 2. Twenty-five minutes after *Salmonella* infection, some of the cells were lysed with 0.1% Triton to release intracellular bacteria. Cell lysates were then plated on LB agar and enumerated after 20 h incubation. The media of the remaining infected cells were replaced by pre-warmed RPMI medium containing 10 µg/ml Gentamicin 25 min post infection.

Figure 8B:
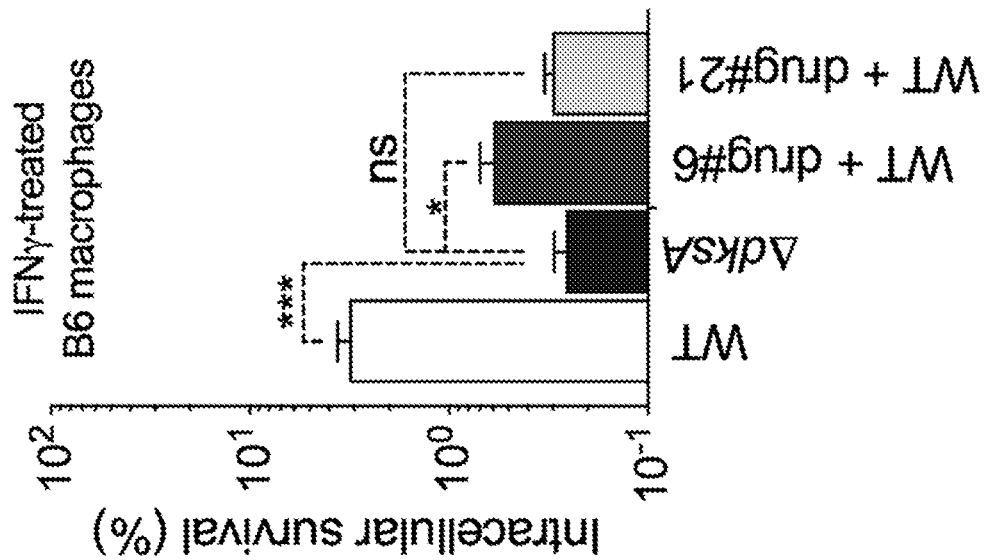
FIGS. 8A and 8B are graphs showing the effects of anti-DksA drugs on persistent populations of intracellular Salmonella.

The remaining infected cells were divided into different groups to be treated with compounds #6 and #21 at the final concentration of 32 µg/ml and 8 µg/ml, respectively. After additional 20 hrs incubation, cells were harvested and lysed. The lysates were plated onto LB agar plates, and subsequently counted after 20 h. Survival percentage is estimated by taking the number of bacteria at the later time point divided by the numbers of bacteria isolated 25 min after infection (FIG. 8B).

Figure 8A:
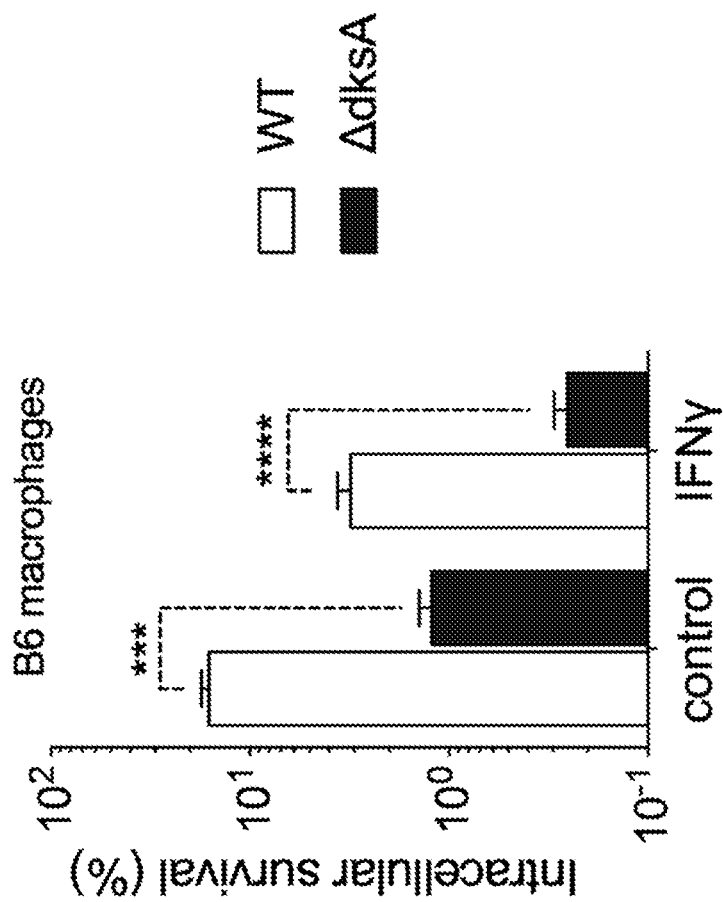

Data shown in FIG. 8A demonstrate that *Salmonella* deficient in dksA are not only more easily killed than wild-type controls in untreated macrophages, but are very susceptible to IFNγ-activated killing and are unable to establish a persistent infection. These findings show that DksA inhibitors prevent formation of persistent *Salmonella* infection and that drugs that inhibit DksA function can be used for treatment of persistent infections as monotherapy (FIG. 8B).

Example 6: Growth and Survival Assays

*Salmonella* strain 14028s was grown overnight at 37° C. with shaking in LB broth. Cell density was measured by spectrometer by following OD600. Cells were centrifuged and washed once with EG Minimal Salts Media (57.4 mM $K_2HPO_4$, 1.7 mM $MgSO_4$, 9.5 mM Citric acid, 16.7 mM $H_5NNaPO_4$, and 0.4% D-Glucose, pH 7.0). The specimens were then resuspended with EG media and adjusted to the final concentration of $1\times10^5$/ml.

One hundred microliters of the cell dilution were plated onto LB agar plate to verify the starting concentration. Ten 5-ml cell culture tubes were prepared, and the diluted cells were transferred to the culture tubes at 1 ml/tube. The first culture tube was reserved as the control. The remaining nine tubes were divided into 3 groups (3 tubes each), which were treated with Nitrofurazone, 4-Nitroquinoline N-oxide, and Mitomycin C at 8 μM, 8 μM, and 0.75 μM, respectively. Within each group, two of the tubes additionally received compounds #21 or #23 at 8 μg/ml and 16 μg/ml, respectively. All tubes were then incubated with shaking at 37° C. for 20 hrs. Cells were collected, diluted, plated on LB agar plates, and subsequently counted. Survival percentages were calculated using bacteria counts divided by starting concentration.

Figure 9:
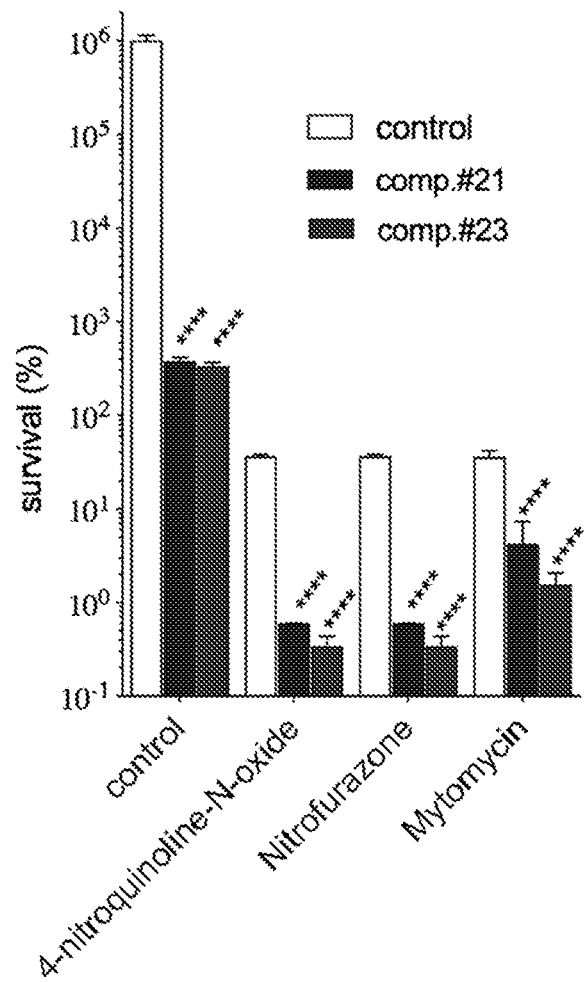
FIG. 9 is a graph showing the synergistic effects of anti-DksA drugs used with antibiotics that target DNA replication.

Compounds #21 and #23 enhanced the anti-*Salmonella* activity of 4-nitroquinoline-N-oxide, nitrofurazone, and mytomycin, demonstrating that anti-DksA drugs sensitize persistent populations to antibiotic killing (FIG. 9). This data demonstrates that, in addition to serving as direct antibiotics, anti-DksA drugs are particularly effective in combination therapies.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of inhibiting growth of and/or killing a bacterium, the method comprising contacting the bacterium with a compound selected from the group consisting of:

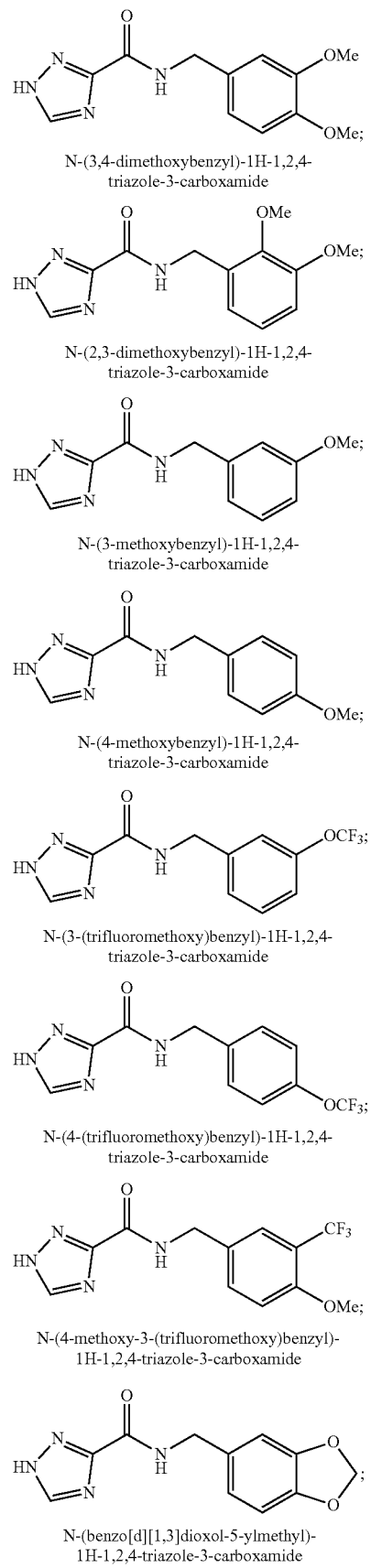

-continued

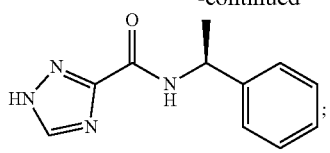

(S)-N-(1-phenylethyl)-
1H-1,2,4-triazole-3-carboxamide

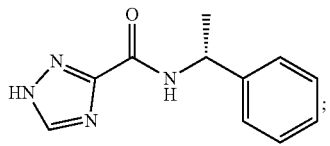

(R)-N-(1-phenylethyl)-
1H-1,2,4-triazole-3-carboxamide

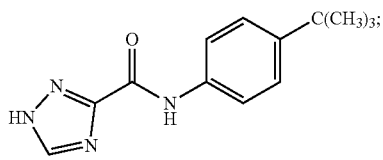

N-(4-(tert-butyl)phenyl)-
1H-1,2,4-triazole-3-carboxamide

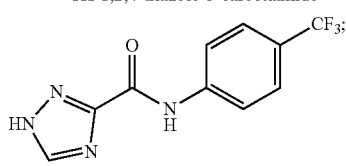

N-(4-(trifluoromethyl)phenyl)-
1H-1,2,4-triazole-3-carboxamide

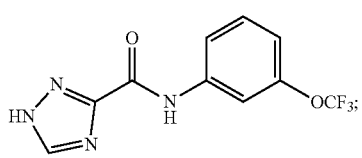

N-(3-(trifluoromethoxy)phenyl)-
1H-1,2,4-triazole-3-carboxamide

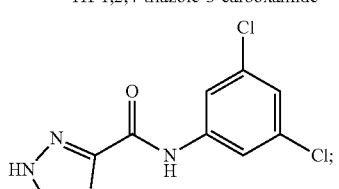

N-(3,5-dichlorophenyl)-
1H-1,2,4-triazole-3-carboxamide

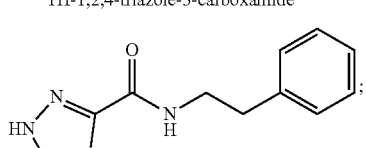

N-phenethyl-1H-
1,2,4-triazole-3-carboxamide

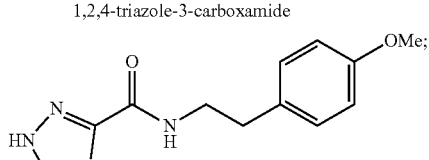

N-(4-methoxyphenethyl)-1H-
1,2,4-triazole-3-carboxamide

-continued

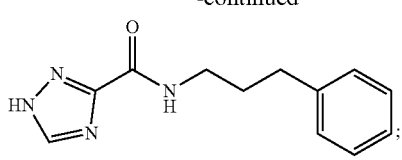

N-(3-phenylpropyl)-1H-
1,2,4-triazole-3-carboxamide

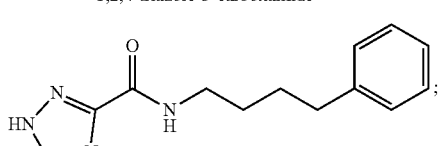

N-(4-phenylbutyl)-1H-
1,2,4-triazole-3-carboxamide

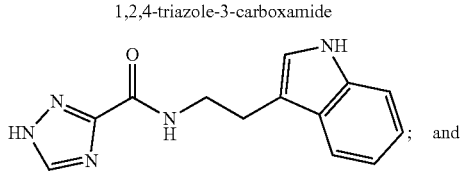

N-(2-(1H-indol-3-yl)ethyl)-1H-
1,2,4-triazole-3-carboxamide

; and

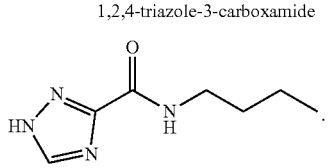

N-butyl-1H-1,2,4-
triazole-3-carboxamide

2. The method of claim 1, wherein the bacterium is gram-negative.

3. The method of claim 2, wherein the bacterium is at least one selected from the group consisting of *Klebsiella, E. coli, Proteus, Serratia, Salmonella, Yersinia, Enterobacter, Pseudomonas aeruginosa, Neisseria gonorrhoeae, Chlamydia trachomatis, Acinetobacter* and *Stenotrophomonas*.

4. The method of claim 1, wherein the bacterium has a DksA protein.

5. A method of treating a bacterial infection in a subject in need thereof, the method comprising administering to the subject a therapeutically effective amount of a compound selected from the group consisting of:

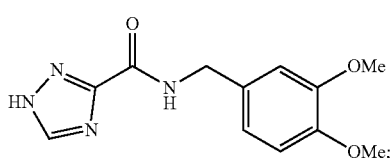

N-(3,4-dimethoxybenzyl)-1H-1,2,4-
triazole-3-carboxamide

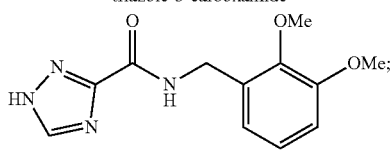

N-(2,3-dimethoxybenzyl)-1H-1,2,4-
triazole-3-carboxamide

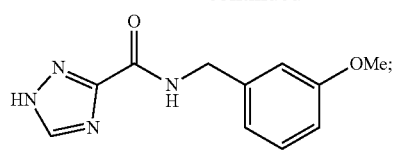

N-(3-methoxybenzyl)-1H-1,2,4-
triazole-3-carboxamide

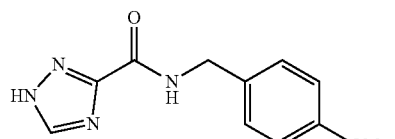

N-(4-methoxybenzyl)-1H-1,2,4-
triazole-3-carboxamide

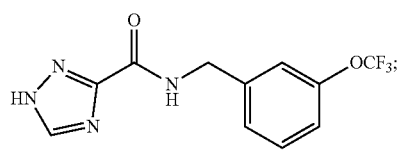

N-(3-(trifluoromethoxy)benzyl)-1H-1,2,4-
triazole-3-carboxamide

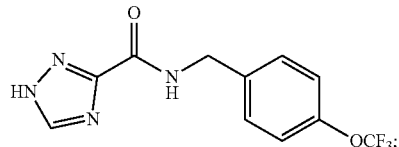

N-(4-(trifluoromethoxy)benzyl)-1H-1,2,4-
triazole-3-carboxamide

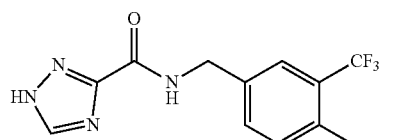

N-(4-methoxy-3-(trifluoromethoxy)benzyl)-
1H-1,2,4-triazole-3-carboxamide

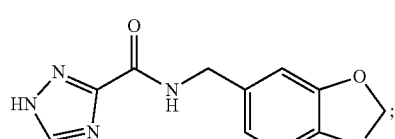

N-(benzo[d][1,3]dioxol-5-ylmethyl)-
1H-1,2,4-triazole-3-carboxamide

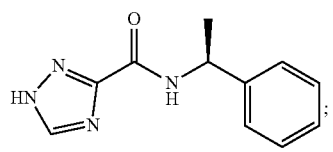

(S)-N-(1-phenylethyl)-
1H-1,2,4-triazole-3-carboxamide

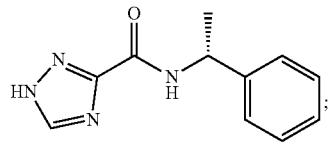

(R)-N-(1-phenylethyl)-
1H-1,2,4-triazole-3-carboxamide

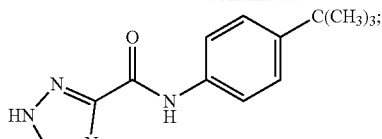

N-(4-(tert-butyl)phenyl)-
1H-1,2,4-triazole-3-carboxamide

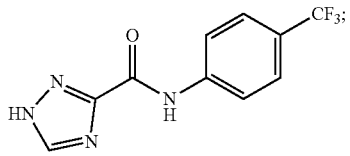

N-(4-(trifluoromethyl)phenyl)-
1H-1,2,4-triazole-3-carboxamide

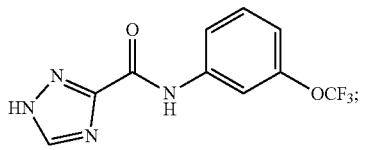

N-(3-(trifluoromethoxy)phenyl)-
1H-1,2,4-triazole-3-carboxamide

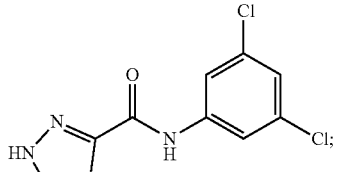

N-(3,5-dichlorophenyl)-
1H-1,2,4-triazole-3-carboxamide

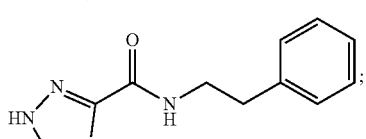

N-phenethyl-1H-
1,2,4-triazole-3-carboxamide

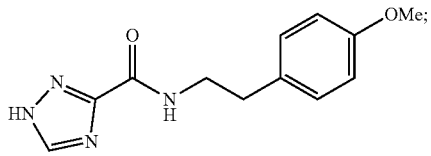

N-(4-methoxyphenethyl)-1H-
1,2,4-triazole-3-carboxamide

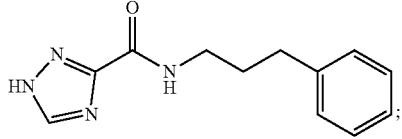

N-(3-phenylpropyl)-1H-
1,2,4-triazole-3-carboxamide

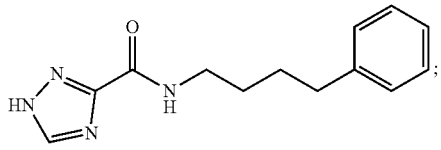

N-(4-phenylbutyl)-1H-
1,2,4-triazole-3-carboxamide

-continued

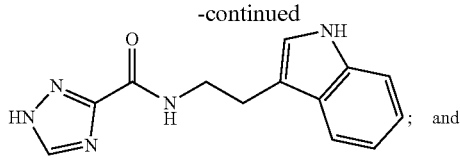

N-(2-(1H-indol-3-yl)ethyl)-1H-1,2,4-triazole-3-carboxamide

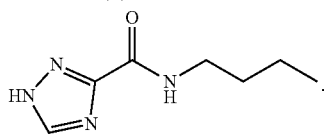

N-butyl-1H-1,2,4-triazole-3-carboxamide

6. The method of claim 5, wherein the bacterium is gram-negative.

7. The method of claim 6, wherein the bacterium is at least one selected from the group consisting of *Klebsiella, E. coli, Proteus, Serratia, Salmonella, Yersinia, Enterobacter, Pseudomonas aeruginosa, Neisseria gonorrhoeae, Chlamydia trachomatis, Acinetobacter* and *Stenotrophomonas*.

8. The method of claim 5, wherein the bacterium has a DksA protein.

9. The method of claim 5, wherein the subject is a mammal.

10. The method of claim 9, wherein the subject is a human.

* * * * *

UNITED STATES PATENT AND TRADEMARK OFFICE
CERTIFICATE OF CORRECTION

PATENT NO. : 12,043,601 B2
APPLICATION NO. : 17/269725
DATED : July 23, 2024
INVENTOR(S) : Michael Fitzpatrick Wempe, Andres Vazquez-Torres and Shaodong Dai It is certified that error appears in the above-identified patent and that said Letters Patent is hereby corrected as shown below:

On the Title Page

Item (71) Applicants, please delete "THE REGENTS OF THE UNIVERSITY OF COLORADO, Denver, CO (US);" and insert --THE REGENTS OF THE UNIVERSITY OF COLORADO, a body corporate, Denver, CO (US)--

Item (73) Assignees, please delete "THE REGENTS OF THE UNIVERSITY OF COLORADO, Denver, CO (US);" and insert --THE REGENTS OF THE UNIVERSITY OF COLORADO, a body corporate, Denver, CO (US)--

Signed and Sealed this
Nineteenth Day of November, 2024

Katherine Kelly Vidal
*Director of the United States Patent and Trademark Office*